(12) United States Patent
Fan et al.

(10) Patent No.: US 7,422,868 B2
(45) Date of Patent: Sep. 9, 2008

(54) MICROBIAL ATP EXTRACTION AND DETECTION SYSTEM

(75) Inventors: Frank Fan, Madison, WI (US); Braeden Butler, Madison, WI (US); Keith V. Wood, Mr. Horeb, WI (US)

(73) Assignee: Promega Corporation, Madison, WI (US)

( * ) Notice: Subject to any disclaimer, the term of this patent is extended or adjusted under 35 U.S.C. 154(b) by 70 days.

(21) Appl. No.: 11/173,092

(22) Filed: Jul. 1, 2005

(65) Prior Publication Data

US 2006/0008860 A1   Jan. 12, 2006

Related U.S. Application Data

(60) Provisional application No. 60/584,971, filed on Jul. 2, 2004.

(51) Int. Cl.
*C12Q 1/02* (2006.01)
*C12N 1/06* (2006.01)

(52) U.S. Cl. .......................................... 435/29; 435/259
(58) Field of Classification Search ........................ None
See application file for complete search history.

(56) References Cited

U.S. PATENT DOCUMENTS

| | | | |
|---|---|---|---|
| 4,080,265 A | | 3/1978 | Antonik |
| 4,246,340 A | | 1/1981 | Lundin et al. |
| 4,303,752 A | | 12/1981 | Kolehmainen et al. |
| 4,349,510 A | * | 9/1982 | Kolehmainen et al. ........ 422/66 |
| 5,004,684 A | | 4/1991 | Simpson et al. |
| 5,258,285 A | * | 11/1993 | Aegidius ........................ 435/8 |
| 5,648,232 A | * | 7/1997 | Squirrell ...................... 435/34 |
| 5,798,214 A | | 8/1998 | Squirrell |
| 5,814,471 A | | 9/1998 | Wood |
| 5,866,348 A | | 2/1999 | Scheirer |
| 5,891,659 A | | 4/1999 | Murakami et al. |
| 5,918,259 A | | 6/1999 | Squirrell |
| 6,174,704 B1 | | 1/2001 | Chu et al. |
| 6,503,723 B1 | | 1/2003 | van Lune et al. |
| 6,548,018 B2 | | 4/2003 | DiCesare et al. |
| 6,599,711 B2 | | 7/2003 | Crouch et al. |
| 6,660,489 B2 | | 12/2003 | Schrecengost et al. |
| 6,696,569 B2 | | 2/2004 | Akhavan-Tafti et al. |
| 2003/0104507 A1 | | 6/2003 | Wood et al. |

FOREIGN PATENT DOCUMENTS

| | | |
|---|---|---|
| EP | 1 211 322 A2 | 5/2002 |
| WO | WO 00/49171 | 8/2000 |
| WO | WO 02/066671 A2 | 8/2002 |

OTHER PUBLICATIONS

Thore et al. Detection of Bacteriuria by Luciferase Assay of Adenosine Triphosphate; Journal of Clinical Microbiology, vol. 1, No. 1 (1975) pp. 1-8.*

Wilson et al. Chelation of Divalent Cations by ATP, Studied by Titration Calorimetry; Analytical Biochemistry, vol. 193, No. 1 (1991) Abstract.*

Kitayama et al. Creation of a Thermostable Firefly Luciferase With pH-Insensitive Luminescent Color; Photochemistry and Photobiology, vol. 77, No. 3 (2003) pp. 333-338.*

Xie et al. Salicylic Acid Induces Rapid Inhibition of Mitochondrial Electron Transport and Oxidative Phosphorylation in Tobacco Cells: Plant Physiology, vol. 120 (1999) pp. 217-225.*

Yang et al. A Convenient One-Step Extraction of Cellular ATP Using Boiling Water for the Luciferin-Luciferase Assay of ATP; Analytical Biochemistry, vol. 306 (2002) pp. 323-327.*

Hamilton-Miller, J.M.T. "Effect of EDTA Upon Bacterial Permeability to Benzylpenicillin", Biochemical and Biophysical Research Communications, vol. 20, No. 6, pp. 688-691, 1965.

Muschel, Louis H. et al., "Antibiotic, Detergent, and Complement Sensitivity of *Salmonella typhi* after Ethylenediaminetetraacetic Acid Treatment", Journal of Bacteriology, pp. 2010-2013, 1968.

Weiser R. et al., "In Vitro Reversal Antibiotic Resistance by Ethylenediamine Tetra-acetic Acid", Nature, vol. 219, pp. 1365-1366, Sep. 28, 1968.

Cleeland R., et al., "Effect of $Mg^2$ and Ethylenediaminetetraacetate on the In Vitro Activity of Coumermycin $A_1$ and Novobiocin Against Gram-Negative Bacteria", Infection and Immunity, vol. 2, No. 4, pp. 371-375, 1970.

Marrie, Thomas J. et al., "Prolonged Survival of Serratia Marcescens in Chlorhexidine", Applied and Environmental Microbiology, vol. 42, No. 6, pp. 1093-1102, Dec. 1981.

Hancock, R. E. W., "Alterations in Outer Membrane Permeability", Annual Review of Microbiology, pp. 237-264, 1984.

Nikaido, Hiroshi, "Outer Membrane", Chapter 5 in *Escherichia coli and Salmonella, Cellular and Molecular Biology*, 2nd Ed., vol. 1, pp. 29-47, 1996.

Chopra, Ian et al., "Tetracycline Antibiotics: Mode of Action, Applications, Molecular Biology, and Epidemiology of Bacterial Resistance", Microbiology and Molecular Biology Reviews, vol. 65, No. 2, pp. 232-260, Jun. 2001.

Morbe JL et al.,"Release of Miniantibodies from *E. coli* cells into the supernatant at low and high cell densities", Microbiol. Res.,152(4):385-94, Dec. 1977; obtained at Internet Address: http/www.ncbi/nlm.nih.gov/entrez/query.fcgi?cmd=Retriev&db+pubmed&dopt=Abstract&list_uids, Sep. 12, 2005.

(Continued)

*Primary Examiner*—Jon P Weber
*Assistant Examiner*—Paul C. Martin
(74) *Attorney, Agent, or Firm*—Brinks Hofer Gilson & Lione; Peter Brunovskis

(57) ABSTRACT

The present invention is directed to compositions and methods for single-step extraction and detection of ATP levels from microbial cells. The disclosed compositions are formulated to efficiently elicit bioluminescent detection of ATP among a broad variety of different microorganisms using a common single-step reagent composition. Additional luminescence-based methods are provided for identifying other useful extracting agents or for screening compounds for their pharmaceutical or biological effects on microbial cells.

26 Claims, 13 Drawing Sheets

OTHER PUBLICATIONS

Akhavan-Tafti H, Lauwers KS et al., 13th International Symposium on Bioluminescence & Chemiluminescence, Symposium Abstract, Luminescence, 2004 John Wiley & Sons, Ltd.

CellTiter-Glo™ Luminescent Cell Viability Assay, Promega Technical Bulletin No. 288, pp. 1-11.

BacTiter-Glo™ Microbial Cell Viability Assay, Promega Technical Bulletin No. 337, pp. 1-12.

PKLight™ "HTS Protein Kinase Assay Kit", Product Catalog, obtained at Internet Address: http://www.cambrex.com/CatNav.asp?oid=890&prodoid+PKLight, Jul. 28, 2003, 1 page.

ViaLight™ MDA Microbial Detection Assay, Instructions for Use, Version MDA 005.0103, 9 pages.

ATP Determination Kit (A-22066) Molecular Probes, Product Information, Revised Apr. 23, 2003, pp. 1-3.

ATP Bioluminescence Assay Kit HS II, Catalog No. 1 699 709, Version 3, Mar. 2004, pp. 1-4.

International Search Report and Written Opinion for PCT/US2005/023545.

Noriaki Hittori et al., "Novel Antibiotic Test by the ATP-Bioluminescence Method Using Filamentous Cell Treatment", *Antimicrobial Agents and Chemotherapy*, vol. 42, No. 6, pp. 1406-1411, Jun. 1998.

\* cited by examiner

| ◆ 25 mM EDTA | ■ 24 mM EDTA | ― 23 mM EDTA |
| 22 mM EDTA | ✱ 0 mM EDTA | |

MICROBIAL ATP EXTRACTION AND DETECTION SYSTEM

This application claims the benefit of priority under 35 U.S.C. § 119(e) to U.S. Provisional Application No. 60/584,971, filed Jul. 2, 2004.

FIELD OF THE INVENTION

The present invention relates to compositions and methods for lysing bacteria and other microbial cells to detect and quantify ATP.

BACKGROUND

One of the characteristics distinguishing live cells from dead cells is the presence of ATP. Because ATP is a substrate in a widely used bioluminescent detection system, it can provide a surrogate marker for cell viability or cell contamination. Methods for extracting and detecting ATP from cells using the luciferin-luciferase system are known in the art. However, depending on the type of cell, the requirements for extraction and detection of ATP may differ. Somatic cells, with their structurally flexible phospholipid bilayer membranes can be readily disrupted with mild detergents to release ATP. Bacteria, yeasts and fungi, with their more rigid cell walls, present a greater challenge.

U.S. Pat. No. 4,303,752 (Kolehmainen et al.) described a process for selective determination of nucleotides (such as ATP) from viable somatic and microbial cells. Kolehmainen et al. developed a multi-step process exploiting the differential permeabilities of somatic and microbial cells using various ionic and non-ionic surface active agents. While somatic cells were found to release ATP following treatment with a non-ionic detergent, such as ethoxylated alkylphenol, bacterial cells were unaffected. This observation provided a means for treating mixed populations of somatic and bacterial cells involving treatment of somatic cells ethoxylated alkylphenol, washing away somatic ATP that was released, and treating the remaining cells (the ATP-containing microbial- and ATP-lacking somatic cells) with a harsher ionic surfactant mixture containing an ethoxylated quaternary amine and an ethoxylated amine to release microbial ATP. In a final step the released ATP was measured in a bioluminescent assay.

Recently, Wood et al. (U.S. 2003/0104507) disclosed a method for detecting ATP in cells using a homogenous reagent composition containing all the components for extracting and detecting ATP from cells in a single step. The reaction components, uniquely formulated to retain the ATP release function without sacrificing luciferase, provided a significant advance in terms of economy and time. However, the disclosed method is not optimal for microbial cells, because of their more rigid cell walls.

One problem associated with the use of harsher permeabilizing agents needed for microbes, such as ionic detergents, is their ability to inactivate the luciferase enzymes. This reagent incompatibility problem necessitates an additional neutralization or dilution step prior to a final luciferase/luciferin addition step to initiate the ATP detection and places a roadblock to development of a single-step ATP extraction/detection reagent composition.

Given the difficulties associated with release and detection of ATP from microbial cells, there is a need in the art for improved reagent compositions and methods for single-step detection of ATP in microbial cells. In addition to the challenges associated with release of ATP from cell wall-carrying cells, microbial cells are typically much smaller than somatic cells. This necessitates further improvements with respect to sensitivity. The present invention provides an advance in application of the single-step ATP detection methodology to microbial cells and is based in part on the discovery that microbial cells exhibit unexpected differences with regard to their ability to support release and detection of ATP.

SUMMARY

The present invention is directed to reagent compositions and methods for extracting and detecting ATP from microbial cells. The invention is based in part on the discovery that reaction conditions for extracting and detecting ATP differs between and among both microbial cells and somatic cells and that reagent compositions may be formulated to facilitate efficient single-step detection of ATP from a broad variety of microbial cells.

In one aspect, the present invention includes a reagent composition including a reaction buffer, at least one ATP extracting agent, a divalent cation, a divalent cation chelator and/or a luciferase/luciferin mixture in which the divalent cation concentration is sufficiently low or sufficiently neutralized by cation chelator to reduce the negative effects of divalent cation on ATP extraction. In one embodiment, the difference between the divalent cation chelator concentration and the divalent cation concentration in the reagent composition is less than about 5 mM. In another embodiment, the concentration of divalent cation chelator is at least one-half of the divalent cation concentration. Divalent cation chelator may be unnecessary in instances where the divalent cation concentration is low (e.g. less than about 5 mM, 2.5 mM or 1 mM). In a particularly preferred embodiment, the chelator concentration is equal to or greater than the divalent cation concentration, the divalent cation is $Mg^{2+}$, the divalent cation chelator is EDTA, and the at least one ATP extracting agent includes cetyltrimethylammonium bromide, chlorohexidine, and a non-ionic detergent, such as Triton-X100.

In another aspect, the present invention includes a method for detecting ATP in microbial cells in which a microbial sample is contacted with a reagent composition that includes a reaction buffer, at least one ATP extracting agent, a divalent cation, and a divalent cation chelator to form a mixture in which the divalent cation concentration is sufficiently low or sufficiently neutralized by cation chelator to reduce the negative effects of divalent cation on ATP extraction, and the level of divalent cation is sufficient for the subsequent luciferase-mediated ATP detection step. The difference between the divalent cation chelator concentration and the divalent cation concentration in the mixture may be less than about 5 mM. Alternatively, the divalent cation chelator concentration may be at least one-half of the divalent cation concentration in the mixture, preferably equal to or even greater in concentration. Divalent cation chelator may be unnecessary in instances where the divalent cation concentration is low (e.g. less than about about 5 mM, 2.5 mM, or 1 mM). In a preferred embodiment, the method is directed to a method for detecting ATP in microbial sample containing or suspected to contain a gram-negative microorganism, such as *E. coli*.

In a further aspect, the present invention includes a method for identifying ATP extracting agents suitable for detecting ATP in a microbial sample in which a composition containing divalent cation, a divalent cation chelator, at least one ATP extracting agent, a luciferase enzyme, and a luciferase substrate are added to the sample to form a mixture; the degree of luminescence is measured to identify a reagent composition suitable for detecting ATP in the sample. Typically, the ATP extracting agent is suitable for detecting ATP in the microbial source if the degree of luminescence is sufficient for detecting ATP in the microbial sample. In a preferred embodiment, the divalent cation is present in the mixture at a concentration of less than about 0.5 mM, more preferably less than about 0.1 mM. The microbial sample may include a gram positive or gram negative bacterium, archaebacterium, fungus or the like.

Alternatively, the microbial sample is contacted with a reagent composition including divalent cation, divalent cation chelating agent, at least one ATP extracting agent, and a luciferase enzyme to form a first mixture having a first divalent cation concentration; contacting the microbial sample to form a second mixture only differing from the first mixture in having a higher divalent cation concentration in the second mixture than in the first mixture; and identifying suitable microbial ATP extracting agents concentration(s) for release and detection of ATP in which the luminescence in the first mixture is higher than the luminescence in the second mixture.

In a further aspect, the microbial ATP extraction/detection system of the present invention may be used to test for microbial cell viability or to identify pharmaceutically active agents (e.g. antibiotic drug candidates) or biologically active agents on the basis of their ability to affect microbial cell viability and/or growth.

DETAILED DESCRIPTION

A. Definitions

Figure 1A:
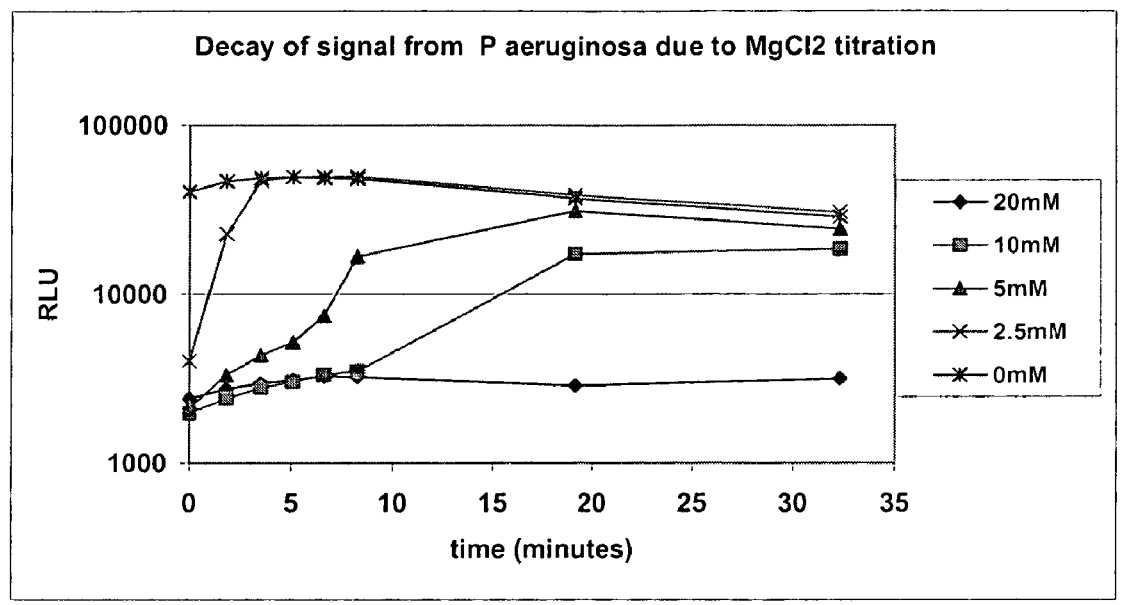
FIG. 1 is graph depicting the kinetics of ATP detection in $P.$ $aeruginosa$ (FIG. 1A) at different $MgCl_2$ concentrations. Purified ATP was used as a control in FIG. 1B.

In order to provide a clear and consistent understanding of the specification and claims, the following definitions are provided. Unless defined otherwise, all technical and scientific terms have the same meaning as is commonly understood by one of skill in the art to which this invention belongs. All cited patents and publications are incorporated by reference in their entirety unless otherwise noted.

An "isolated" or "purified" luciferase is one that has been identified and separated and/or recovered from a component of its natural environment.

The term "sample" as used herein, is used in its broadest sense. A sample is a composition suspected of containing ATP that is analyzed using the invention. While often a sample is known to contain or suspected of containing a cell or a population of cells, optionally in a growth media, or a cell lysate, a sample may also be a solid surface, (e.g., a swab, membrane, filter, particle), suspected of containing an attached cell or population of cells. It is contemplated that for such a solid sample, an aqueous sample is made by contacting the solid with the reagent composition of the invention or to another aqueous solution to which the reagent composition of the invention is added. Filtration is desirable in some cases to generate a sample, e.g., in testing a liquid or gaseous sample by a process of the invention. Filtration is preferred when a sample is taken from a large volume of a dilute gas or liquid.

The term "reagent composition" is used herein to designate one or more components for extracting and/or detecting ATP from a sample. The reagent composition may include some or all or the components sufficient for extracting and/or detecting ATP from a sample.

The term "reaction mixture" as used herein, refers to the contents present (or resulting) after contacting a sample containing ATP or suspected to contain ATP with one or more reagent compositions collectively sufficient to extract and detect ATP from the sample.

The term "detection," as used herein, refers to quantitatively or qualitatively determining the presence or absence of a component within the sample.

The term "ATP extracting agent" as used herein, refers to any compound or combination of compounds that alters cell membrane or cell wall permeability or disrupts the integrity of (i.e., lyses or causes the formation of pores in) the membrane and/or cell wall of the microbial source to effect extraction or release of ATP. Generally, ATP extracting agents may include a variety of agents, including, but not limited to antibiotics, such as polymyxin B (e.g., polymyxin B1 and polymyxin B2), polymyxin-beta-nonapeptide (PMBN), and chlorohexidine (CHEX); alkylglucoside or alkylthioglucoside, such as Octyl-β-1-thioglucopyranoside (see U.S. Pat. No. 6,174,704 herein incorporated by reference in its entirety);

nonionic detergents, such as Triton-X100 (TX-100); betaine detergents, such as carboxypropylbetaine (CB-18); quarternary ammonium salts, such as trimethyloctadecyl ammonium bromide (TMA-18); protamines; amines, such as triethylamine (TEA) and triethanolamine (TeolA); and cationic, antibacterial, pore forming, membrane-active, and/or cell wall-active polymers, such as polylysine, nisin, magainin, melittin, phopholipase $A_2$, phospholipase $A_2$ activating peptide (PLAP); bacteriophage; and the like. See e.g., Morbe et al., Microbiol. Res. (1997) vol. 152, pp. 385-394.

The term "stable signal" is defined as a luminescent signal exhibiting less than 50% loss of luminescence per half hour relative to the luminescence at the time the luciferase reaction was initiated.

The term "signal:noise ratio" (S:N) is defined by the equation S:N=(mean luminescence of sample minus mean of background)/standard deviation of background luminescence.

The present invention is drawn to reagent compositions and methods for detecting and quantifying ATP levels from microbial cells and is based on the unexpected discovery that reaction conditions for release and detection of ATP from microbial cells can be realized without requiring a neutralization step prior to or incorporated within a subsequent luminescence detection step. The present invention discloses reagent compositions capable of facilitating stable luminescent detection of ATP from a wide range of microbial cells. Further, by carefully selecting an appropriate combination of reaction components, efficient single-step release of ATP can be obtained from virtually any bacterial or microbial cell.

B. Magnesium Reversal Effect

Figure 1B:
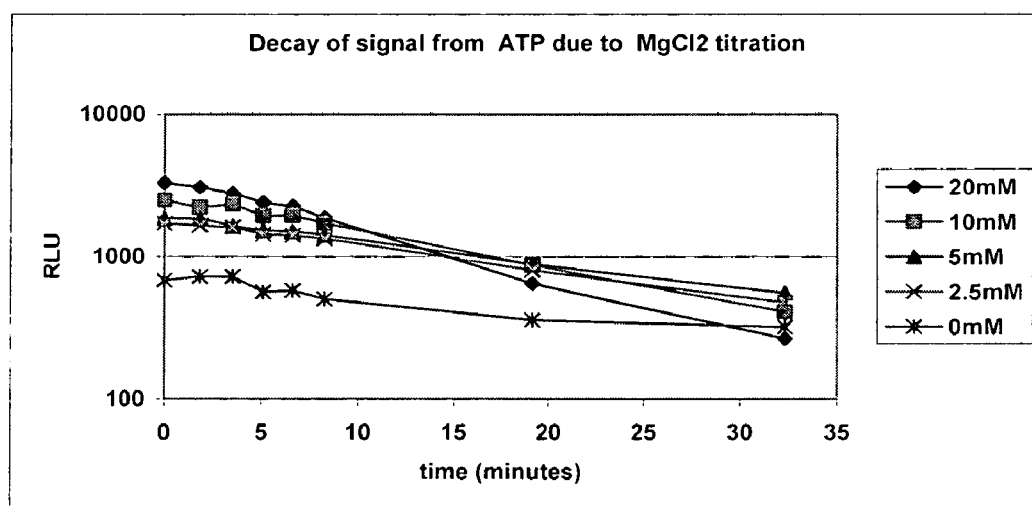
Figure 2:
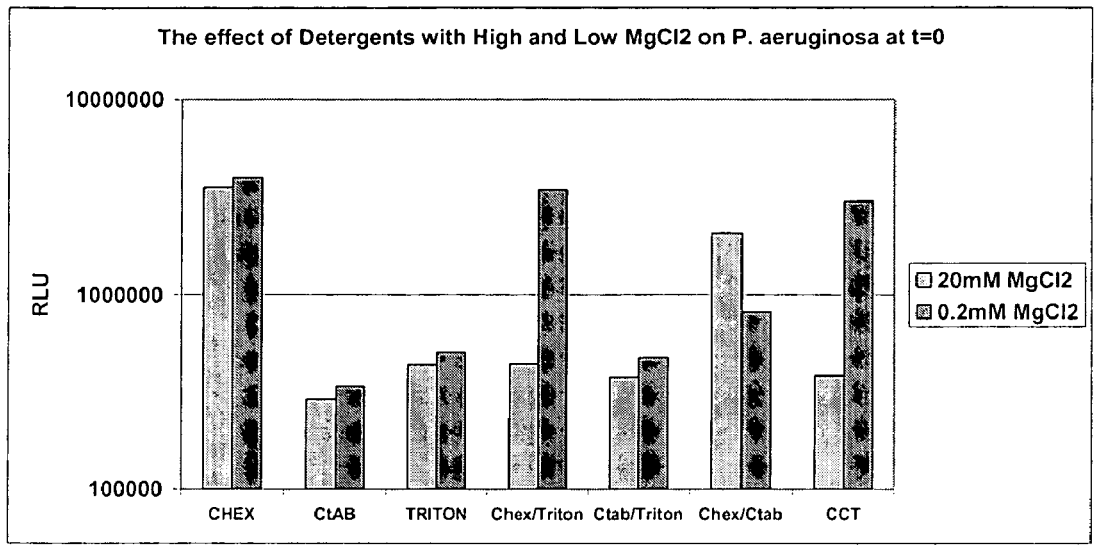
FIG. 2 is a graph is a graph depicting the effects of different ATP extracting agent combinations on ATP detection in $P.$ $aeruginosa$ at low (−; 0.2 mM) and high (+; 20.0 mM) divalent cation ($MgCl_2$) concentrations.
Figure 3:
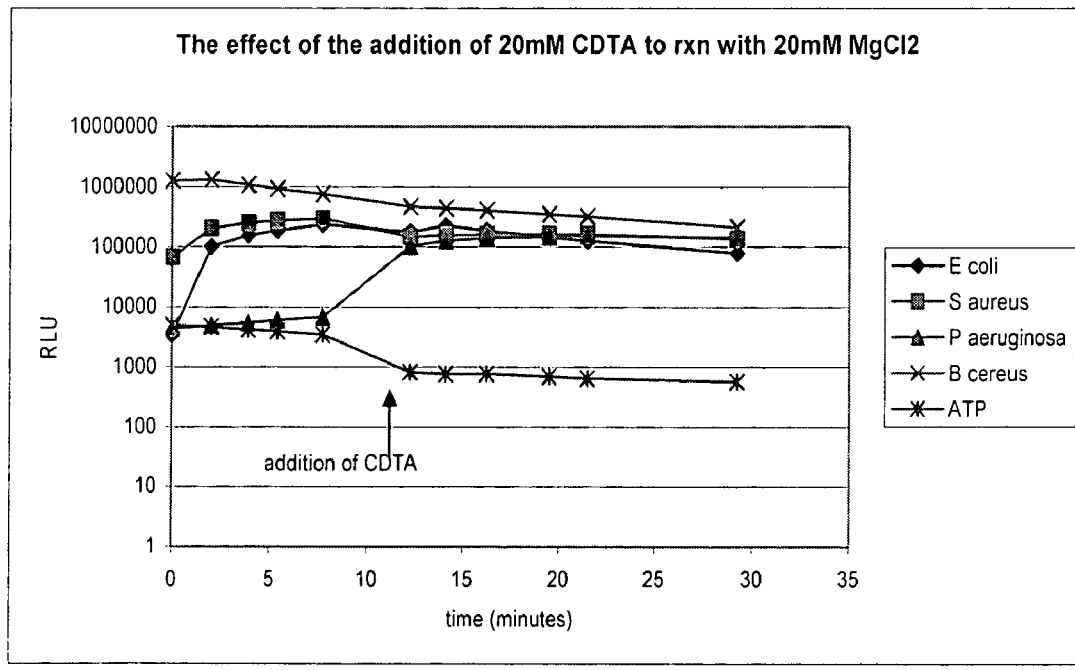
FIG. 3 is a graph depicting neutralization of inhibitory divalent cation effects using chelating agents to mimic the higher luminescence obtained under low divalent cation concentration conditions in various microorganisms ($E.$ $coli,$ $S.$ $aureus,$ $P.$ $aeruginosa,$ and $B.$ $cereus$). CDTA was added to reaction mixtures containing 20 mM $MgCl_2$ at t=12 minutes (final concentration=20 mM CDTA).

In one aspect of the present invention, the inventors have found that non-optimal divalent cation concentrations can impede effective release and detection of ATP from some microbial cells. Typical luciferase-mediated ATP detection methodologies utilize reagent compositions having divalent cation concentrations as much as 10-20 mM and divalent cation chelator concentrations of about 1-2 mM (see e.g., Wood et al., U.S. 2003/0104507). FIG. 1 describes an experiment demonstrating differences in the kinetics of ATP detection as a function of divalent cation concentration for *B. cereus* (FIG. 1A) and *P. aeruginosa* (FIG. 1B). Even though divalent cations are essential for ATP detection, the results from this experiment document the surprising finding that better luminescence in microbial cells may actually be obtained using lower than expected amounts of divalent cation. Moreover, the inventors of the present invention have surprisingly found that bioluminescence resulting from use of certain ATP extracting agent combinations can be selectively enhanced by reducing the free divalent cation (e.g. $Mg^{2+}$) concentration in the reagent composition or reaction mixture with a divalent cation chelator, such as EDTA (FIG. 2). This "magnesium reversal effect" is further supported by experiments in which addition of chelator compounds, such as CDTA was found to activate luminescence (FIG. 3). The inventors of the present invention have further documented the unexpected benefit for extraction and detection of ATP when using a divalent chelator at a higher concentration than the divalent cation present in the ATP extraction/detection reagent composition or reaction mixture (or simply using lower divalent cation amounts with or without chelator). By optimizing reagent compositions to exploit these observations, efficient ATP release and detection could be obtained from a wide variety of microbial sources using the same reagent composition.

While not wishing to be bound by theory, it is believed that structural characteristics of different microorganisms may account for inhibitory effects of divalent cations with regard to ATP release. For example, the cell wall of gram positive and gram negative bacteria differ with respect to the density and composition of their peptidoglycan layers and by the presence or absence of an outer lipid bilayer membrane. The cell wall of gram-positive bacteria appears as a broad, dense wall (20-80 nm thick) consisting of numerous interconnecting layers of peptidoglycan making up 60-90% of the gram-positive cell wall. Interwoven in the cell wall are teichoic acids and various glyoproteins. In contrast to the gram-positive cell wall, the gram negative cell wall includes 2-3 layers of peptidoglycan-containing inner wall (2-3 nm thick) making up only 10-20% of the gram-negative cell wall and an outer membrane (about 7 nm thick) composed of phospholipids, lipopolysaccharides (LPS), and proteins. The LPS in the outer membrane of gram-negative bacteria is thought to add strength to the outer membrane, in a manner similar the glycoproteins and teichoic acids of the gram-positive cell wall. In contrast to bacteria, the cell walls of yeasts and fungi are even stronger than bacterial cell walls, containing other substances such as chitin, to protect the fragile cell membranes therein.

The outer membrane of gram-negative bacteria provides a barrier function strengthened by divalent cations that stabilize the electrostatic repulsion between negatively charged groups in neighboring LPS molecules. (Nikaido, *Outer Membrane*, In *Escherichia coli* and *Salmonella*," ASM Press, Washington D.C., pp. 29-47). The barrier function explains the relative impermeability of certain antibiotic compounds, such as nafcillin, a hydrophobic penicillin. Addition of EDTA, a divalent cation chelator, and/or bulky amines, such as Tris, is thought to inhibit the tight association between LPS molecules. Divalent cation chelators, such as EDTA or CDTA can destabilize the outer membrane and facilitate the momentary rupture and release of cellular components (such as ATP) when using the ATP extraction agents of the present invention.

Inasmuch as divalent cations are capable of inhibiting ATP release on the one hand, they are essential components of the luminescent reaction for detecting ATP. For maximal sensitivity in ATP detection, concentration of divalent cations, particularly magnesium, are typically used in concentrations greater than about 10 mM (See FIG. 1B). A single-step reagent composition for extracting and detecting ATP in samples containing microbes must negotiate these conflicting requirements for divalent cations. Moreover, the inventors have found that optimal extraction and detection of ATP from microbes can be achieved rapidly, within 10 minutes, preferably within 5 minutes after addition of the reagent composition to the sample. Determining the optimal amount(s) of divalent cation or cation chelator to use in the reagent composition will depend on a variety of factors, including but not limited to, the type and structure of microorganism; the degree to which divalent cations stabilize components of the cell wall and/or cell membrane; the amount of ATP, cation, and/or cation chelator already present in the microbial sample; and the amount or stability of luciferase in the reagent composition or reaction mixture.

C. Reagent Compositions

1. ATP Extracting Agents

One aspect of the invention includes the use of one or more ATP extracting agents to promote release of ATP from a microbial cell. Microbial ATP extracting agents may include a variety of agents capable of permeabilizing a microbial cells wall and/or membranes to facilitate ATP release including, but not limited to antibiotics, such as polymyxin B (e.g., polymyxin B1 and polymyxin B2), polymyxin-beta-nonapeptide (PMBN), and chlorohexidine (CHEX); alkylglucoside or alkylthioglucoside, such as Octyl-β-D-1-thioglucopyranoside (see U.S. Pat. No. 6,174,704 herein incorporated by reference in its entirety); nonionic detergents, such as nonionic ethoxylated alkylphenols, including but not limited to the ethoxylated octylphenol Triton X-100 (TX-100) and other ethoxylated alkylphenols; betaine detergents, such as carboxypropylbetaine (CB-18); quarternary ammonium salts, such as Cetyltrimethylammoniumbromide (CTAB); trimethyloctadecyl ammonium bromide (TMA-18); protamines; amines, such as triethylamine (TEA) and triethanolamine (TeolA); and cationic, antibacterial, pore forming, membrane-active, and/or cell wall-active polymers, such as polylysine, nisin, magainin, melittin, phopholipase $A_2$, phospholipase $A_2$ activating peptide (PLAP); bacteriophage; and the like. See e.g., Morbe et al., Microbiol. Res. (1997) vol. 152, pp. 385-394, and U.S. Pat. No. 4,303,752 disclosing ionic surface active compounds which are incorporated herein by reference in their entirety.

ATP extracting agents are preferably chosen not to inactivate the luciferase enzymes of the present invention. For microbes requiring harsher agents for ATP release (e.g., ionic detergents etc.), modified luciferases exhibiting enhanced stability in the presence of these agents are particularly preferred, such as those disclosed in U.S. 2003/0104507, the entire contents of which is hereby incorporated by reference.

In one embodiment of the invention, the ATP extracting agent(s) include CTAB, a quaternary ammonium salt. In preferred embodiments, CTAB is present in the reagent composition at a concentration between about 0.04%-0.15% (w/v). In another embodiment, the ATP extracting agents may include CHEX and an ethoxylated alkylphenol, such as Triton X-100. In preferred embodiments, CHEX is preferably between about 0.04%-0.16% (w/v) and the ethoxylated alkylphenol is present between about 0.25%-1.0% (w/v). In a particularly preferred embodiment, the reagent composition may include more than one ATP extracting agent. One preferred embodiment includes CHEX, (between about 0.04%-0.16% (w/v)); an ethoxylated alkylphenol, such as Triton X-100 (between about 0.25%-1.0% (w/v)); and a quaternary ammonium salt, such as CTAB, (between about 0.02%-0.08% (w/v)).

It is fully anticipated that the most preferred concentration(s) or concentration range(s) functional in the methods of the invention will vary for different microbes and for different ATP extracting agents and may be empirically determined using the methods described in the subject application or commonly known to those skilled in the art.

2. Divalent Cations

The beetle luciferase-luciferin reaction is dependent not only on ATP, but also on divalent cations. Therefore, to facilitate luciferase activity, divalent cations are typically supplied (unless already present in the sample). Divalent cations include magnesium, calcium and manganese. Divalent cations may be supplied as salts or halides such as sulfate, sulfonate, gluconate, carbonate, chloride and bromide. For example magnesium cations may be supplied as magnesium chloride, magnesium sulfate, magnesium gluconate, magnesium acetate, magnesium bromide, magnesium carbonate, etc. Preferably, the divalent cation is selected from the chloride or sulfate salts of magnesium.

Because the permeability of certain cell membranes or walls may be negatively affected by the presence of divalent cations, divalent cation concentrations may be empirically formulated for a given microorganism or a given extraction/detection system to provide the proper balance between e.g., cell release of ATP and ATP detection.

Further, given that divalent cation chelators have the ability to neutralize the negative effects of divalent cations on ATP extraction, divalent cation concentrations may be adjusted depending on the level of divalent cation chelator present in a reagent composition or reaction mixture. When divalent cation chelator is low (e.g. less than about 5 mM, 2.5 mM or 1 mM), divalent cation concentrations will be accordingly lower, preferably less than 2.5 mM, more preferably between 0.2-1 mM. When divalent cation chelator is higher (e.g. 2-20 mM), however, divalent cation concentration will be accordingly higher, preferably with a concentration less than or equal to the concentration of the divalent cation chelator.

3. Divalent Cation Chelator Agents

Divalent cation chelator agents include, without limitation, salts of ethylenediamine tetraacetic acid (EDTA), ethylene glycol tetraacetic acid (EGTA), and 1,2-Cyclohexanedinitrilotetraacetic acid (CDTA), nitriloacetic acid (NTA), citric acid, sodium gluconate, gluconic acid, lignosulfonates, and mixtures thereof. Preferably, the chelator agent is selected from the group consisting of EDTA, EGTA and CDTA, due to their general availability and relatively low cost. Suitable levels of divalent cation chelator may be empirically determined on the basis of providing levels sufficient to neutralize the negative effects of divalent cation on ATP extraction, but not to the extent that they prevent the cation-dependent, luciferase-catalyzed ATP detection.

Generally, the chelator concentration is at least about 50% of the divalent cation concentration, preferably about 60%, 70%, 80%, 90%, or 95% of the divalent cation concentration. More preferably, the chelator concentration is about equal to or greater than the divalent cation concentration. In a particularly preferred embodiment, the chelator concentration is in a range of about 20 to 25 mM. Divalent cation chelator may be unnecessary in instances where the divalent cation concentration is low (e.g. less than about 5 mM, 2.5 mM, or 1 mM).

One of skill in the art will recognize, however, that different chelators may have different chelating capacities depending on the pH. Thus, the outer parameters of the present invention include a degree of variability in chelator concentrations for chelators commensurate with providing a chelator capacity comparable to that of EDTA under otherwise identical luciferase assay reaction conditions (at e.g., pH 7.0-8.0 etc.). In other words, divalent cation chelator amounts may be adjusted to provide a chelating capacity comparable or exceeding the chelating capacity of EDTA under otherwise identical single-step ATP reaction conditions (all other reagents and reagent concentrations same, except for divalent chelator) or may be adjusted in an amount sufficient to balance the negative and positive effects of divalent cations on extraction and detection of ATP, respectively.

4. Luciferases/Luciferin

At their most basic level, luciferases are defined by their ability to produce luminescence. More specifically, luciferases catalyze the oxidation of a substrate, luciferin, thereby producing oxyluciferin and photons. Luciferases, whose catalytic products include light, offer sensitivity, a detectable product, and facile measurement of ATP. Any ATP-dependent luminescence-producing enzyme is contemplated for use in the reagent compositions and methods of the present invention.

To date, at least five classes of luciferases have been identified (Jones et al., 1999; Thomson et al., 1997). Of these, beetle luciferases, such as that of the common firefly (family Lampyridae), form a distinct class with unique evolutionary origins (McElroy et al., 1969; White et al., 1969; White et al., 1975). Beetle luciferases are often referred to as firefly luciferases in the literature; however, firefly luciferases are actually a subgroup of the beetle luciferase class. Beetle luciferases may be purified from the lanterns of the beetles themselves or from protein expression systems well known in the art (Baldwin and Green, 2000; Beny and Dolivo, 1976; Branchini et al., 1980; Filippova et al., 1989).

All luciferases, luciferase variants, luciferase fragments and variant luciferase fragments that catalyze an ATP-dependent reaction and generate luminescence are contemplated for use in the invention, including, but not limited to those disclosed in U.S. 2003/0104507, the entire contents of which is hereby incorporated by reference in its entirety. Beetle luciferases, particularly firefly luciferase from the North American firefly *Photinus pyralis*, are well known in the art. The *P. pyralis* luciferase (LucPpy) consists of approximately 550 amino acids of $M_r$ 61 kDa as calculated by the protein encoded by the nucleotide sequence of the gene. Other firefly luciferases in accordance with the present invention include *Photuris pennsylvanica* firefly luciferase (LucPpe2; 545 amino acid residues; GenBank 2190534, (Ye et al., 1997), as well as various mutant luciferases disclosed in U.S. 2003/0104507, which are derived from LucPpe2 (e.g., LucPpe2 m78 (also known as 78-0B10); LucPpe2 m90 (also known as 90-1B5); LucPpe2 m133 (also known as 133-1B2); LucPpe2m146 (also known as 146-1H2); and various commercially available luciferases, such as UltraGlo™ Luciferase (Promega). Methods for making LucPpe2m78, LucPpe2m90, LucPpe2m133, and LucPpe2m146 are disclosed in U.S. 2003/0104507, and are hereby incorporated by reference in their entirety.

Isolated and/or purified luciferases are typically used in the present invention. Contaminant components derived from their natural environment, capable of interfering with diagnostic or therapeutic uses, may include enzymes, hormones, and other proteinaceous or non-proteinaceous materials. One technique to ascertain purity is applying SDS-PAGE analysis under non-reducing or reducing conditions using Coomassie blue or silver stain. Luciferases may be isolated from native luciferase-producing sources or from a recombinant cell expressing an exogenous luciferase-encoded polynucleotide. Techniques for producing and/or purifying luciferase enzymes are well known to those of skill in the art.

The naturally-occurring substrate for beetle luciferases is firefly luciferin, a polytherocyclic organic acid, D-(-)-2-(6'-hydroxy-2'-benzothiazolyl)-$\Delta^2$-thiazolin-4-carboxylic acid (luciferin). Luciferin may be isolated from nature (e.g. from fireflies) or synthesized. Synthetic luciferin can have the same structure as the naturally occurring luciferin or can be a variant or derivitization, so long as it functions analogously (Bowie et al., 1973; Branchini, 2000; Craig et al., 1991; Miska and Geiger, 1987; Yang and Thomason, 1993). Exemplary luciferin derivatives for use in the present invention include, but are not limited to, 6-deoxyaminoluciferin, D-luciferin methyl ester, D-luciferyl-L-phenylalanine, D-luciferyl-L-N α-argimine, D-luciferin-O-sulphate and D-luciferin-O-phosphate (Miska and Geiger, 1987), esters of luciferases that are hydrolyzed or acted upon by esterases to luciferin by components in a sample (Craig et al., 1991; Yang and Thomason, 1993). Other examples of useful luciferin analogs include naphthyl- and quinolyllucierin, which emit light in the green and red light spectra respectively (Branchini et al., 1989). There are multiple commercial sources for luciferin (e.g., Promega Corp. Madison, Wis.; Molecular Probes, Eugene, Oreg.).

The beetle luciferase-catalyzed reaction producing a luminescent signal from the luciferase-luciferin reaction requires luciferase enzyme, luciferin, adenosine triphosphate (ATP), magnesium (or other divalent cation), and molecular oxygen. In the initial reaction, luciferin and ATP react to form luciferyl adenylate with the elimination of inorganic pyrophosphate. The luciferyl adenylate remains tightly bound to the catalytic site of luciferase. When this foil of the enzyme is exposed to molecular oxygen, the enzyme-bound luciferyl adenylate is oxidized to yield oxyluciferin in an electronically excited state. The excited oxidized luciferin emits light on returning to the ground state:

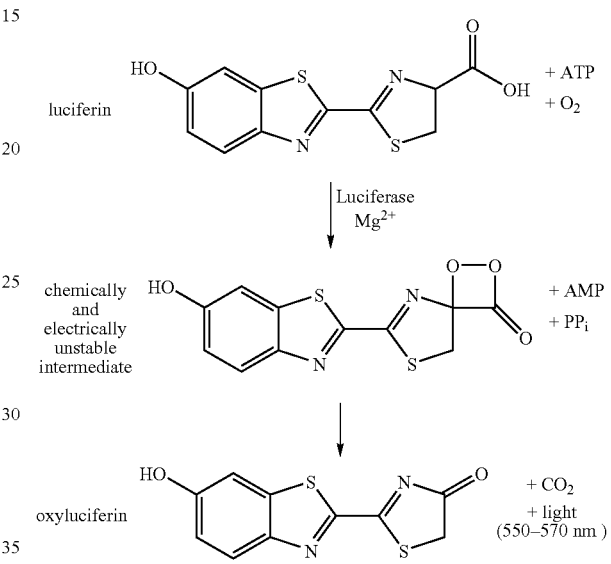

ATP analogues (e.g., dATP) are also capable of carrying out the above reaction. Moreover, other divalent cations may substitute for magnesium in the above reaction (e.g., $Mn^{2+}$ or $Ca^{2+}$). Since oxygen is a reactant of the reaction, the reaction cannot be conducted under anaerobic conditions. However, it is generally unnecessary to provide oxygen over and above that present in the air. Reactions can take place in closed vessels, provided there is sufficient oxygen in the reaction solution.

Most luciferase-luciferin reactions generate a flash of light that is short lived. However, some of the luciferases preferred for use with the invention, e.g., LucPpe2m146 and LucPpe2m90 luciferases, under the conditions of the invention generate a "glow-type" luminescent signal with less than 50% loss of luminescence per hour after the reagent composition is combined with the sample to form a mixture. Preferred luciferases, luciferase variants, luciferase fragments, or variant luciferase fragments within the scope of the present invention include those capable of preserving their stability within the milieu of the reagent composition and retaining their ability to generate a stable luminescence when in the context of that same reagent composition.

To facilitate completion of the luciferase-catalyzed reaction, a substrate for the luciferase, such as luciferin, may be included in the reagent composition. Some embodiments within the scope of the present invention may eliminate the luciferin and allow a user to supply a luciferin of his/her choice; alternatively, the luciferin may be separately provided for addition to the other reaction components. The type of luciferin provided may vary, but it must be a substrate for the particular luciferase used in a given application.

The ability to create a homogeneous, single-step extraction and detection reagent composition is not necessarily dependent on the chemo or thermostability of the luciferase, as native enzymes may work in such compositions too. However, the use of thermostable luciferases is preferred, because they are less susceptible to loss of activity from other components in the formulation, such as the ATP extracting agents and may provide greater selectivity and/or sensitivity, and more compatibility with a wider range of reaction conditions (i.e. ambient and/or higher temperatures). Similarly, to the extent that "chemostable luciferases" are better able to retain activity or increase sensitivity and/or performance in the presence of compounds or conditions (as compared to e.g., wild type enzymes), they will be preferred.

Preferred luciferases for use in the reagent compositions, mixtures, or methods of the invention generate a stable signal, i.e., such luciferases, when used in a luciferase reaction, yield luminescence with enhanced duration defined as less than 50% loss of luminescence per half hour relative to the luminescence at the time the luciferase reaction was initiated. Preferred luciferases include those that which maintain at least about 30% (preferably at least about 50%, 60%, 70%, 80%, 90%, 95% or 99%) enzymatic activity for at least one hour, preferably for at least two hours, still more preferably at least four hours (as measured by luminescence).

5. ATPase Inhibitors or Inhibitors of ATP Metabolism

Microbial cells may include substances capable of distorting the amount of ATP present in a cell over time. This may be due to the presence of ATPases, ATPase inhibitors and/or inhibitors of ATP-generating enzymes. Because the ATP concentration is determined at a specific time, inappropriate activity associated with ATP generation or loss, if left unchecked, may lead to an over-estimation of the ATP concentration present in the microbial cells.

To accurately measure ATP levels in a sample, it is preferable to inhibit enzymes capable of degrading microbial ATP pools or inappropriately generating new sources of ATP. Failure to incorporate appropriate inhibitors, may lead to an inaccurate determination of ATP concentration. Exemplary ATPase inhibitors include ATP extracting agents of the present invention (such as CTAB), cationic or non-ionic detergents, or any of the ATPase inhibitors disclosed in U.S. 2003/0104507. Inhibitors such as DTAB may inactivate certain ATPases, while other molecules such as sodium fluoride (NaF) may inactivate phosphatases affecting the activity of microbial kinases involved in regulating ATP metabolism.

Exemplary inhibitors of ATP-generating enzymes may include kinase or phosphatase inhibitors (such as NaF), as disclosed in U.S. 2003/0104507. In preferred embodiments, reagent compositions of the present invention may comprise NaF at concentrations of at least about 0.2 mM, preferably at least about 1 mM, more preferably at least about 2 mM. Other inhibitors of ATP-generating enzymes may include other kinase inhibitors, such as vanadate, AMP, DAPP (Bostick et al., 1982) and dichloroacetic acid (Kiechle et al., 1980).

Use of inhibitors to prevent inappropriate production or loss of ATP may be particularly useful in high-throughput applications where many sample plates need to be read over an extended period of time, providing a greater opportunity for distorting the original ATP level present in the sample.

6. Buffers

Selection of appropriate buffers depends on pH buffering capacity and interaction with the luciferase-luciferin reaction. Any buffers that maintain suitable pH for the working solution and do not interfere with the luciferase-luciferin reaction are contemplated. The preferred pH range is between about pH 4.5 and about pH 9.0, more preferably between about pH 6.0 and about pH 8.0. In addition to MES and citrate buffers, typical buffers may include phosphate buffered saline (PBS), Tris, N-(2-Hydroxyethyl)piperazine-N'-(2-ethanesulfonic acid) (HEPES), piperazine-1,4-bis(2-ethanesulfonic acid) (PIPES), borate, and any other buffer known to those of skill in the art may be suitable. Typical buffering agents may include Tricine, HEPPS, HEPES, MOPS, Tris, Glycylglycine, and phosphate salts used to maintain proper pH and ionic strength. Preferred buffer concentration may range from about 50 mM to 200 mM.

7. Defoamers

Defoaming agents are desirable to prevent loss of sample and/or cross-contamination of samples due to foaming. Addition of defoamer may also facilitate the dispensing of product during manufacturing or use. Suitable defoaming agents include those available under the tradename MAZU® (PPG Industries, Gurnee, Ill.), and may be organic or silicone based. Selection of defoamers may depend on their ability to eliminate foam without interfering with the luciferase-luciferin reaction.

8. Other Agents

The reagent composition may also include a stabilizing agent or volatilility control agent. The stabilizing agent or volatility control agent may be any compound that stablizes the luciferase from degradation and/or aids in lyophilization of luciferase and/or luciferin. Suitable enzyme stabilizing agents include, but are not limited to, bovine serum albumin (BSA); BSA substitutes, such as PRIONEX™ (Pentapharm, Ltd., Basel Switzerland); gelatin; and detergents (preferably non-ionic detergents, most preferably THESIT).

The reagent composition of the present invention may also include substances known to enhance the duration of luminescence (extended the half-life of detection), including, but not limited to, sodium pyrophosphate (NaPPI; e.g. at about 25 mM); co-enzyme A (CoA); thiol reagents, such as dithiothreitol and P mercaptoethanol (Wood, U.S. Pat. No. 5,283,179, 1994; Wood, U.S. Pat. No. 5,650,289, 1997); metal ion chelator agents (in addition to their use in ATP extraction/detection) or protease inhibitors (Scheirer, U.S. Pat. No. 5,618,682, 1997; Scheirer, U.S. Pat. No. 5,866,348, 1999); or high concentrations of salts (Van Lune and Trer Wiel, WO 00/18953, 2000).

D. Methods for Extracting and Detecting ATP in Microbial Cells

The methods, compositions and kits of the invention provide for the simple qualitative or quantitative detection of ATP (or ATP analogue which can function as a luciferase substrate) in a microbial sample. Generally, a simple qualitative experiment demonstrating luminescence in a sample is indicative of the presence of ATP.

In one aspect, the present invention includes a method for detecting ATP in microbial cells in which a microbial sample is contacted with a reagent composition containing a reaction buffer, at least one microbial ATP extracting agent, a divalent cation, and a divalent cation chelator in which the difference between the divalent cation chelator concentration and the divalent cation concentration is less than about 5 mM. Alternatively, the divalent cation chelator concentration in the reagent composition or reaction mixture may be at least one half the divalent cation concentration, preferably equal or even higher. However, divalent cation chelator may be unnecessary in instances where the divalent cation concentration is low (e.g. less than about 5 mM, 2.5 mM, or 1 mM). Preferably, a detectable luminescent signal is produced within 5 or 10 minutes after contacting the microbial sample with the reagent composition. Essentially, any of the reagent compositions described in this disclosure are contemplated for use in the methods of the present invention.

Contacting the microbial sample with the reagent composition facilitates extraction or release of ATP from the microbial cells for reaction with the appropriate bioluminescence reagents present in the reagent composition thereby producing a readily detectable bioluminescent signal. The microbial sample may constitute a purified microbial sample, a mixed population of microbial cells, or a source material suspected to contain microbial cells. In a preferred embodiment, the present invention is directed to methods for extracting and detecting ATP from *E. coli* or from microbial source materials suspected of containing *E. coli*.

A suitable luminescent signal may be generated using a reagent composition containing e.g., at least one ATP extracting agent, such as a cationic or non-cationic detergent; a divalent cation, such as magnesium; a divalent chelating agent, such as EDTA; a source of luciferase, such as LucPpe2 m78, LucPpe2m90, LucPpe2m133 or LucPpe2m146; and one or more luciferase substrates, such as luciferin (which may be reconstituted from a lyophilized preparation or other appropriate luciferin-analogue substrate). The reagent composition may additionally include one or more inhibitor(s) of ATP-generating enzymes, enzyme stabilizing agents, defoaming agents, etc.

1. Microbial Cell Sources

In one aspect, the present invention provides a method for extracting and detecting ATP in a microbial sample or in a sample suspected to contain a microbial sample, such as a bacterium, yeast or other fungus. There are a variety of microbial sources suitable for use in accordance with the present invention, including but not limited to eubacteria (both gram-positive bacteria, gram-negative bacteria), archaebacteria, yeast or fungi. For example, the reagent compositions of the present invention have been found to work with a variety of different microbial organisms, including but not limited to gram negative bacteria, such as *Escherichia coli, Pseudomonas aeruginosa, Enterobacter cloacae, Flavobacterium okeanokoites, Haemophilus influenzae, Proteus vulgaris, Salmonella typhimurium, Yersinia enterocolitica*, and *Francisella philomiragia*; Gram-positive bacteria, such as *Staphylococcus aureaus, Enterococcus faecalis, Streptococcus pneumoniae, Bacillus subtilis, Bacilus cereus, Arthrobacter luteus*; and eukaryotic microorganisms, such as *Saccharomyces cerevisiae* and *Candida albicans*. In a preferred embodiment, the sample contains or is suspected to contain *E. coli* or *P. aeruginosa*. Although the methods of the invention may be used with a sample containing any amount of ATP, it is preferable to use a sample containing a non-saturated amount of ATP (i.e., a range where luminescence is linearly proportional to the concentration of ATP).

The microbial sample may be anything suspected of containing microbes, such as cell lysates, intact cells, biopsies, foods, beverages, swabs wiped on surfaces such as those of animals, plants, or inanimate objects, and the like. Control samples may include a known ATP concentration to generate a standard curve facilitating a quantitative determination of ATP levels in a sample.

A cell lysate comprises cellular components that are no longer organized into a recognizable intact cellular architecture. Cell lysates may have soluble and insoluble components, either of which may be removed before using the lysate. Lysates may be prepared by any means, including physical disruption using sonication, a dounce, mortar and pestle, freeze-thaw cycling, or any other device or process that destroys the physical integrity of cells; or lysis by detergents, such as those in which LucPpe2m146 retains activity, such as zwitterionic and nonionic detergents, or cationic detergents DTAB or CTAB. Preferably, the cell lysate is produced in such a way that the integrity of the ATP concentration is preserved at the time the cells are harvested.

2. ATP Extraction

Efficient extraction or release of ATP from microbial sources may depend on the structural constraints presented by the microbial source. These circumstances may necessitate balancing the amount of divalent chelator compounds to reverse divalent cation-mediated stabilization while sufficient levels of divalent cation to promote bioluminescent detection of ATP. The selection of appropriate ATP extracting agents for extracting and detecting ATP may be empirically determined for a given microbial source. Preferably the selection of these compounds will be predicated on efficient extraction of ATP and retention of ATP detecting activities (e.g., luciferase activity etc.) for single-step extraction and ATP detection in accordance with the present invention.

3. ATP Detection

A beetle luciferase-luciferin reaction results in the generation of light ("luminescence"). Because the beetle luciferase-luciferin reaction is ATP-dependent, luciferase can be used to assay for ATP. The reaction is remarkably sensitive, allowing ATP to be detected in a sample containing as little as $10^{-16}$ moles ATP or less. The compositions, methods and kits of the invention permit a user to quantify the amount of ATP in a sample by quantifying the amount of luminescence. The invention is applied to a sample of interest, and also to samples containing known amounts of ATP (controls). The signal generated from a sample of unknown ATP concentration may be correlated with signals generated from internal controls (e.g. addition of a known amount of ATP to a sample and measuring the subsequent luminescence) or external standard curves, generated by measuring the luminescence of several samples of known ATP concentrations and plotting them graphically. Such methods are known to skilled artisans. (Moyer and Henderson, 1983; Ronner et al., 1999; Stanley, 1989; Wood et al., 1989).

The luminescence generated by a luciferase reaction is typically detected with a luminometer, although other detection means may be used. To measure luminescence and thereby determine the reagent composition activity, the relative light unit (RLU) value generated by the luciferase reaction at a timepoint of interest after the reagent composition is combined with a sample may be measured. The presence of light greater than background level indicates the presence of ATP in the sample. A background level of luminescence may be measured under the same reaction conditions in which the sample exists (e.g. reagent composition etc.), but absent the sample. Positive control reactions involving ATP may be employed to facilitate a determination of ATP amounts present in a sample. These and other control reactions may be determined by one of skill in the art.

Preferred luciferases for use in the compositions and methods of the present invention generate a stable luminescent signal, pronounced in duration, exhibiting less than 50% loss of luminescence per half-hour relative to the luminescent signal generated at the time the luciferase reaction was initiated. Preferred luciferases for use in the compositions and methods of the invention may have enhanced thermostability properties and/or may possess kinetic properties favorable for multiple analyses of a sample over time or the analysis of many samples over time, including, but not limited to one hour after initiation of the luciferase reaction, more preferably two hours and most preferably four hours or more after initiation.

Quantifying the amount of emitted light may enable quantitation of the amount of ATP in a sample, and thereby the quantity of living microbial cells. Quantitative ATP values are realized, for example, when the quantity of light emitted from a test sample is compared to the quantity of light emitted from a control sample or to a standard curve determined by using known amounts of ATP and the same luciferase, substrate, and reaction conditions (i.e. temperature, pH, etc.). It is understood that quantification involves subtraction of background values. Qualitative ATP values are realized when the luminescence emitted from one sample is compared to the luminescence emitted from another sample without a need to know the absolute amount of ATP present in the samples, e.g., a comparison of samples in the presence or absence of a test compound. Many such experiments can readily be designed by one of ordinary skill in the art.

Preferred embodiments in accordance with the present invention are directed to methods of ATP detection using single-step reagent compositions containing a complete set of components to facilitate extraction and detection of ATP. However, reagent compositions containing ATP extracting agents of the present invention may be used independent of the luciferase and luciferin reagents for lysing cells first, prior to the addition of neutralizing agents (e.g. buffers) and/or exogenous luciferase and/or luciferin agents in a final ATP detection step, in accordance with other "two-step" ATP detection methodologies known to those of skill in the art.

4. Cell Viability

The presence of ATP is a reflection of active metabolic processes, characteristic of viable cells. The compositions, methods and kits of the present invention can therefore be used to assay cell viability (Cree, 1998; Jassim et al., 1990; Petty et al., 1995). An accurate measure of cell viability allows for the accurate assessment of the effects of substances on cells; other applications relating to cell viability are known to those of skill in the art. Determining cell viability may be useful in evaluating e.g., cytotoxicity, cell proliferation, necrosis, alterations in cellular metabolism etc.

The microbial samples used to evaluate cell viability may be native, viable cells, or may include cell lysates (as a surrogate marker for cell viability) or any other microbial source materials suspected of containing cells, suspected of being derived from cells, or predicted to reflect viability of the microbial source materials.

5. Assay Kits

An assay kit is contemplated for use in accordance with the present invention and may include the components for making the homogeneous lysis and detection reagent and a set of instructions for use. Preferably, the kit may include a lyophilized source of luciferin/luciferase and a vial of reconstitution buffer containing the ATP extracting agent(s) to make the homogeneous lysis and detection reagent. The reconstitution buffer may be supplied with cations and/or chelators at a fixed concentration or these components may be supplied separately, allowing the user to add divalent cations and/or chelators at a concentration appropriate for use, depending on the particular microbial cell source materials (e.g. individual cell, population etc.).

E. Method for Identifying Reagent Compositions Suitable for Lysing and Detecting ATP in a Bacterial Sample Because different microorganisms exhibit differences in the extent to which they can support a single-step cell lysis—ATP detection process on the basis of structural differences impacting upon this process, in another aspect the present invention provides a method for identifying appropriate reaction conditions suitable for efficient one step lysis and detection of ATP in a particular microorganism or group of microorganisms. In particular, the present invention provides an assay for evaluating or determining an optimal balance between microbial ATP extracting agents, divalent cations and divalent chelator compounds capable of effecting, individually or collectively, the extraction and detection of ATP.

In a preferred embodiment, the present invention provides a method for identifying ATP extracting agent(s) suitable for extraction and detection of ATP in a microbial sample in which (1) a first reagent composition including a first concentration of divalent cation, a divalent cation chelating agent, one or more microbial ATP extracting agent(s), a luciferase enzyme, and luciferase substrate (e.g. luciferin) are combined with a bacterial sample in growth media to produce a first mixture producing a first luminescent signal; and (2) a second reagent composition including a higher concentration of divalent cation than in the first reagent composition, a divalent cation chelating agent, one or more microbial ATP extracting agents, a luciferase enzyme, and luciferase substrate (e.g. luciferin) are combined with the same bacterial sample to produce a second mixture producing a second luminescent signal; where the second reagent composition is suitable for extracting and detecting ATP in the bacterial sample if the first luminescent signal from the first mixture is greater than the second luminescent signal resulting from the second mixture.

Preferably, the divalent cation concentration in the first reagent composition is preferably at least about 10-fold, more preferably at least about 25-fold and still more preferably at least about 100-fold less concentrated than the divalent cation concentration in the second reagent composition. The divalent cation concentration in the first reagent composition may range between about 0 and 2 mM, between about 0.05 mM and 0.5 mM, between about 0.1 and 0.3 mM or be about 0.2 mM. Preferably, the divalent cation concentration in the second reagent composition is between about 20 mM and 200 mM, between about 5 mM and 50 mM, between about 10 mM and 30 mM or about 20 mM.

A variation of the above method may be used to identify reagent compositions suitable for efficiently extracting and detecting ATP from a broad variety of microbial cells. Briefly, this method may involve preparing a reagent composition including luciferase (e.g. thermostable, chemostable or native), luciferin, a fixed $Mg^{2+}$ concentration (e.g. at 5 mM) and buffer; adding a putative ATP extracting agents of interest to the reagent composition and examine the comparative differences in luminescence in the present of either exogenous ATP (positive control) and a collection of different microbial cell sources. In one embodiment, the microbial cell sources may include a variety of different microorganisms representing several classes, including but not limited to Gram negative bacteria, Gram positive bacteria, Archaebacteria and fungi. In another embodiment, the microbial cell sources may include a variety of microorganisms specific for a particular microbial class (e.g. Gram negative bacteria, Gram positive bacteria, Archaebacteria, or fungi). The ATP extracting agent of choice should have minimal impact on the luminescence of ATP control samples, but provide sufficient extraction and generation of a stable luminescence signal (e.g. half-life of at least 24 minutes. Several ATP extracting agents may be individually tested or combined and their dosage effects evaluated in a matrix format to identify the best combination and concentration for each active compound. The effect of $Mg^{2+}$ could be further evaluated by titrating in various concentrations of $Mg^{2+}$, while fixing all other components in the reagent compositions equal.

F. Uses for Detection of ATP in Microbial Cells

1. Determining the Presence of Viable Microbial Cells or Microbial Contamination A principal application of the present invention is for determining the relative viability of microbial cell samples, microbial cell populations, or suspected sources of microbial contamination using the methods disclosed above.

2. Evaluating Pharmaceutically Active or Biologically Active Compounds

Use of cell viability assays in accordance with the present invention may be further applied to the development and testing of pharmaceutically active or biologically active agents. In a preferred embodiment, the compositions, methods and kits of the present invention may be used to evaluate the efficacy of antibiotic candidate compounds or to test the effect of compounds, such as inorganics, small organics, peptides, proteins and polypeptides, on bacterial metabolism (Aiginger et al., 1980; Andreotti et al., 1995; Bradbury et al., 2000; Cree and Andreotti, 1997; Crouch et al., 1993; Kangas et al., 1984). Measurement of cell viability following treatment of microbial cells with pharmaceutically active or biologically active agents (e.g. antibiotics etc) may provide a means for screening and identifying novel pharmaceutically or biologically active agents negatively affecting microbial growth.

For example, microbial cultures in a suitable culture apparatus (e.g. multiwell plate etc.) may be treated with a pool of candidate antibiotic agents (in parallel with untreated control cultures), grown for a time sufficient to microbial growth, and tested for ATP (luminescence assay) using the compositions and methods of the present invention. Generally, a candidate antibiotic agent will be found to exhibit antibiotic activity if the luminescence detected from the untreated control culture is higher than the luminescence from the treated culture. Conversely, a candidate antibiotic agent will typically be found to not have antibiotic activity if the luminescence is equivalent (or even higher) in the treated culture, as compared to the untreated control culture.

A further application of the present invention provides a method for screening antimicrobial peptides analogous to those used in innate immunological defense mechanisms (see e.g., Lehrer and Ganz, Curr. Opin. Immunol., 11(1):23-27, 1999). This method uses a modification of the method described in part E. to identify antimicrobial peptides capable of disrupting microbial cells, in which antimicrobial peptides (or suitable peptide libraries) are substituted for the ATP extracting agents in part E. above. Selected microbial targets (such as antibiotic resistant microorganism) can be treated with e.g., peptide libraries in place of the ATP extracting agents and screened for bioluminescence on the basis of promoting efficient extraction and detection of ATP to identify potential microbicidal agents having a selective ability to lyse microbial cells. The method need not be limited to screening of peptides, however. A variety of different chemical or biochemical compounds may be tested to identify candidate agents exhibiting a selective ability to lyse microbial cells on the basis of results obtained using the disclosed ATP assay system. The following examples are intended to illustrate the present invention without limitation.

EXAMPLES

Example 1

Kinetics of ATP Detection in a Microbial Cell at Different $MgCl_2$ Concentrations The kinetics of ATP detection in a microbial cell was evaluated using a luciferase reagent composition comprised of a reconstitution reagent (200 mM HEPES, pH 7.5 (Sigma), $MgCl_2$ (0 mM, 2.5 mM, 5 mM, 10 mM or 20 mM), 0.08% CTAB (Sigma), 0.16% CHEX (Sigma), 1% Triton-X100 (Sigma), 2 mM sodium fluoride (Sigma), 25 µM NaPPI (Sigma)) and substrate (4 mM citrate, mM luciferin, 0.4% PRIONEX™ (Pentapharm, Ltd), ~0.08 mg/ml thermostable luciferase, 1 mM magnesium sulfate, and 1.25 mM CDTA). Either 100 µl of a P. aeruginosa culture or 100 µl of a $1\times10^{-9}$ M ATP stock solution (control) was added to 100 µl of the luciferase reagent composition and luminescence was measured periodically over a 35 minute time period. P. aeruginosa was tested at approximately $10^6$ cells per well. The results of this analysis (FIG. 1) highlight differences in ATP detection as a function of divalent cation concentration.

Example 2

Detection of ATP in the Presence of Different ATP Extracting Agents

The effects of different ATP extracting agent combinations on ATP detection was tested at low (0.2 mM) and high (20.0 mM) divalent cation concentrations. P. aeruginosa were treated with different ATP extracting agents in the presence of "high" (+; 20 mM) or "low" (−; 0.2 mM) concentrations of $MgCl_2$ in a BacTiter-Glo™ reagent composition (0.358 mg/ml UltraGlo™ Luciferase (Promega), 6 mM beetle luciferin (Promega) 200 mM HEPES (Sigma), 0.08% CTAB (Sigma), 0.16% CHEX (Sigma), 1% Triton-X100 (Sigma), 2 mM NaF (Sigma), 25 µM NaPPI (Sigma)). 100 µl of a P. aeruginosa culture was added to 100 µl of the BacTiter-Glo™ reagent composition and luminescence was measured. P. aeruginosa was tested at approximately $10^6$ cells per well. The results of this analysis (FIG. 2) demonstrate a "magnesium reversal" effect characterized by increased luminescence at an equivalent point in time frame (e.g. at t=0 min.) when reducing the level of magnesium in the reagent composition or mixture from 20 mM to 0.2 mM.

Example 3

Stimulation of ATP Detection Following Addition of a Divalent Chelator Agent

To demonstrate that neutralization of divalent cations with chelating agents can mimic the higher luminescence obtained under low divalent cation concentration conditions, E. coli, S aureus, P. aeruginosa, and B. cereus cultures were treated with a luciferase reagent composition comprised of a reconstitution reagent (200 mM HEPES (Sigma), 20 mM $MgCl_2$, 0.08% CTAB (Sigma), 0.16% CHEX (Sigma), 1% Triton-X100 (Sigma), 2 mM NaF (Sigma), 25 µM NaPPI (Sigma)) and substrate (4 mM citrate, 5 mM luciferin, 0.4% PRIONEX™ (Pentapharm, Ltd), ~0.08 mg/ml thermostable luciferase, 1 mM magnesium sulfate, and 1.25 mM CDTA). Either 100 µl of bacterial culture or 100 µl of a $1\times10^{-9}$ M ATP stock (control) was added to 100 µl of the reconstitution reagent and luminescence was measured periodically over a 35 minute time period. The microbial cultures were tested at approximately $10^6$ cells per well. Additional CDTA was added at t=12 minutes to each of the samples (final concentration=20 mM CDTA). The results of this analysis (FIG. 3) indicate that CDTA is capable of neutralizing the inhibitory effects of divalent cations in *P. aeruginosa*.

Example 4

Detection of ATP in the Presence of Divalent Cation Chelator Agents

Figure 4A:
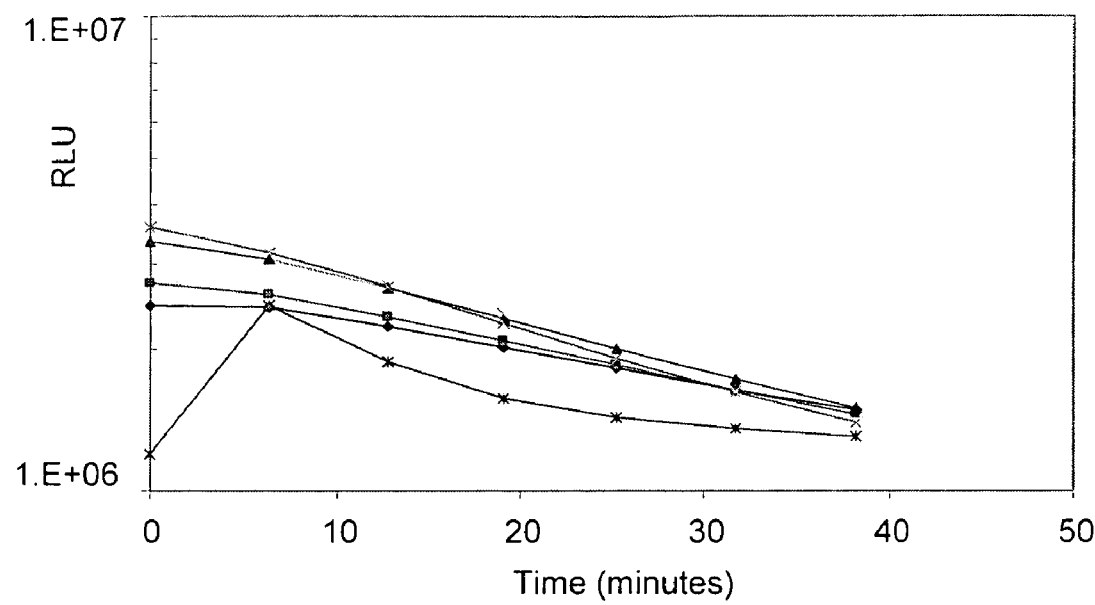
FIG. 4 is a graph depicting the effect of increasing chelator concentrations (EDTA at 0 mM, 22 mM, 23 mM, 24 mM and 25 mM) on the detection of ATP in $E.$ $coli$ (FIG. 4A) or $P.$ $aeruginosa$ (FIG. 4B) in the presence of a 20 mM divalent cation ($MgCl_2$) concentration.
Figure 4B:
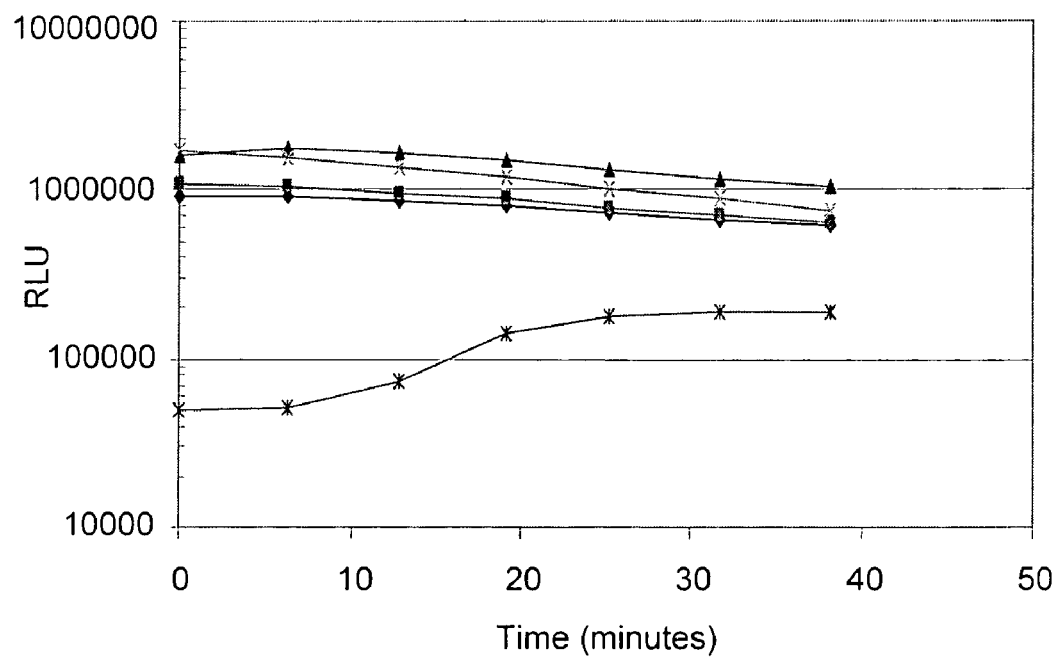

To demonstrate the detection of ATP in the presence of divalent cation chelator agents, a reconstitution reagent composition was prepared (200 mM HEPES (Sigma), 0.08% CTAB (Sigma), 0.16% CHEX (Sigma), 1% Triton-X100 (Sigma), 2 mM NaF (Sigma), 25 µM NaPPI (Sigma), 20 mM $MgCl_2$ (Sigma)) containing varying concentrations of EDTA (0 mM, 22 mM, 23 nM, 24 mM and 25 mM). Luciferase reagent compositions were then generated by mixing the reconstitution reagent compositions with substrate (4 mM citrate, 5 mM luciferin, 0.4% PRIONEX™ (Pentapharm, Ltd), ~0.08 mg/ml thermostable luciferase, 1 mM magnesium sulfate, and 1.25 mM CDTA). 100 µl of *E. coli* (FIG. 4A), *P. aeruginosa* (FIG. 4B) or a $1\times10^{-9}$M ATP stock solution (not shown) was added to 100 µl of the luciferase reagent composition and luminescence was measured periodically over a 40 minute time period. The bacterial cultures were tested at approximately $10^6$ cells per well. The results of this analysis (FIG. 4A, 4B) indicate that inhibitory divalent cation effects may be titrated out using divalent chelator concentrations optimized to promote an appropriate balance between release and detection of ATP.

Example 5

Figure 5A:
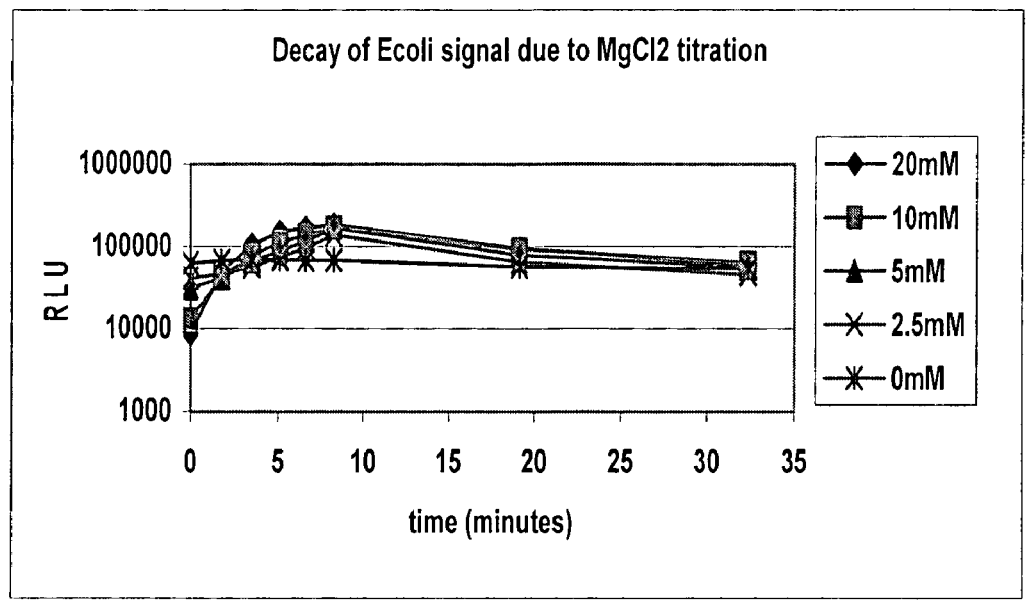
FIG. 5 is a graph depicting the kinetics of ATP detection in different bacteria ($E.$ $coli$ (FIG. 5A), $S.$ $aureus$ (FIG. 5B), $P.$ $aeruginosa$ (FIG. 5C) and $B.$ $cereus$ (FIG. 5D) at various divalent cation ($MgCl_2$) concentrations (0 mM, 2.5 mM, 5 mM, 10 mM, 20 mM).
Figure 5B:
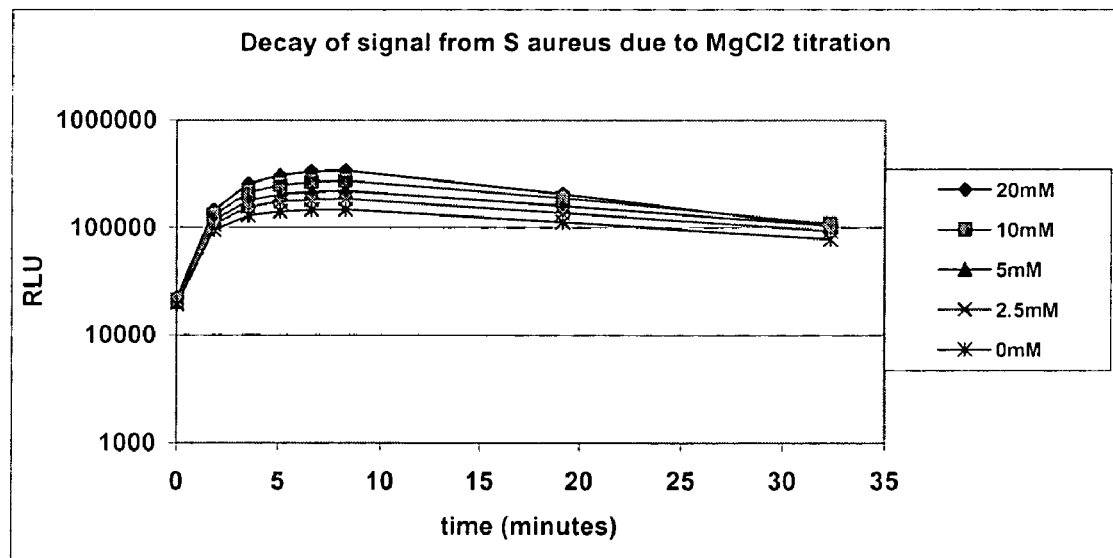
Figure 5C:
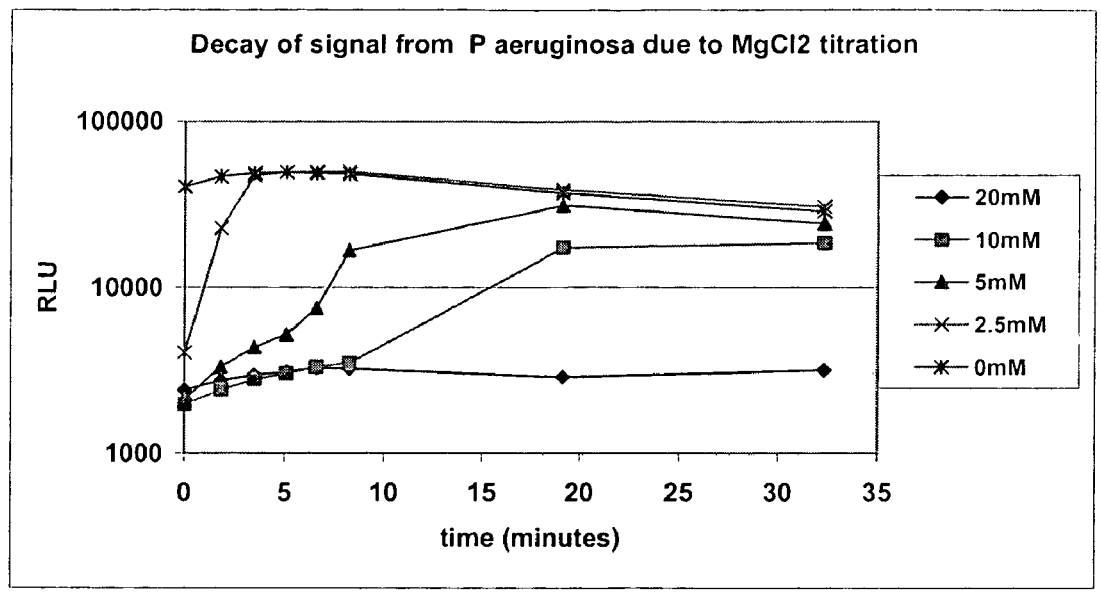
Figure 5D:
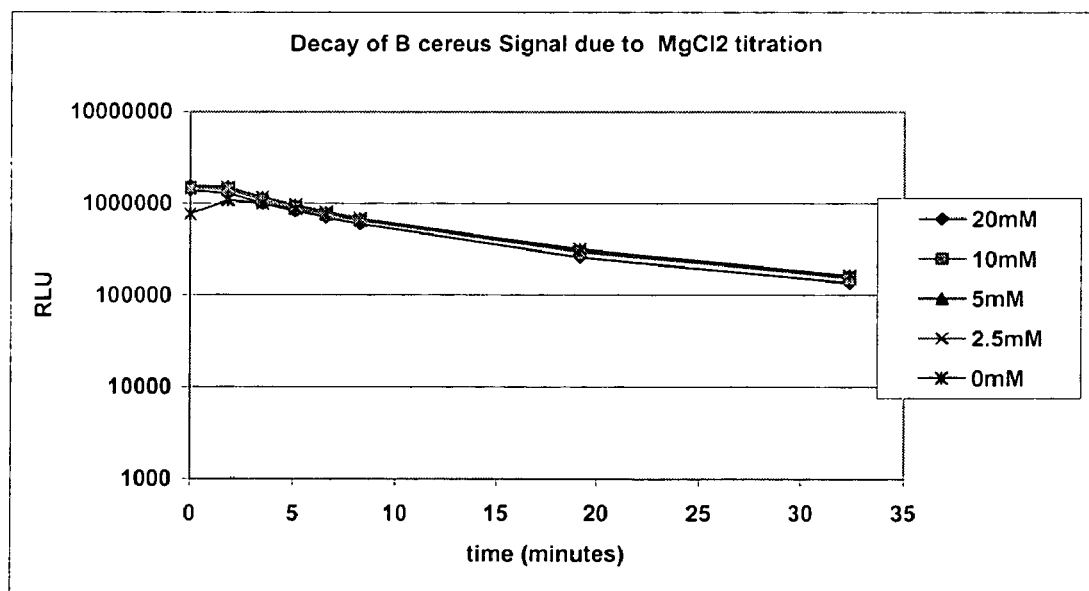

Effects of Different Divalent Cation Concentrations on Detection of ATP Among Different Microbial Cells To determine the effects of divalent cation concentration on detection of ATP among different bacteria, a reconstitution reagent was prepared (200 mM HEPES (Sigma), 0.08% CTAB (Sigma), 0.16% CHEX (Sigma), 1% Triton-X100 (Sigma), 2 mM NaF (Sigma), 25 µM NaPPI (Sigma), and added to varying concentrations of $MgCl_2$ (0 mM, 2.5 mM, 5 mM, 10 mM and 20 mM)) and a substrate (4 mM citrate, 5 mM luciferin, 0.4% PRIONEX™ (Pentapharm, Ltd), ~0.08 mg/ml thermostable luciferase, 1 mM magnesium sulfate, and 1.25 mM CDTA). *E. coli* (FIG. 5A), *S aureus* (FIG. 5B), *P. aeruginosa* (FIG. 5C) and *B. Cereus* (FIG. 5D) were tested at approximately $10^6$ cells per well. A solution of purified ATP was also tested as a control (not shown). Either 100 µl of bacterial culture or 100 µl of a $1\times10^{-9}$ ATP M stock solution was added to 100 µl of reagent and luminescence was measured periodically over a 35 minute time period. The results of this analysis (FIG. 5A-5D) highlight differences in ATP detection depending on the microorganism and divalent cation concentration.

Example 6

Kinetics of ATP Detection at Low (0.2 mM) and High (20 mM) Divalent Cation Concentrations Using a Panel of ATP Extracting Agents in *E. coli* and *P. aeruginosa*

Figure 6A:
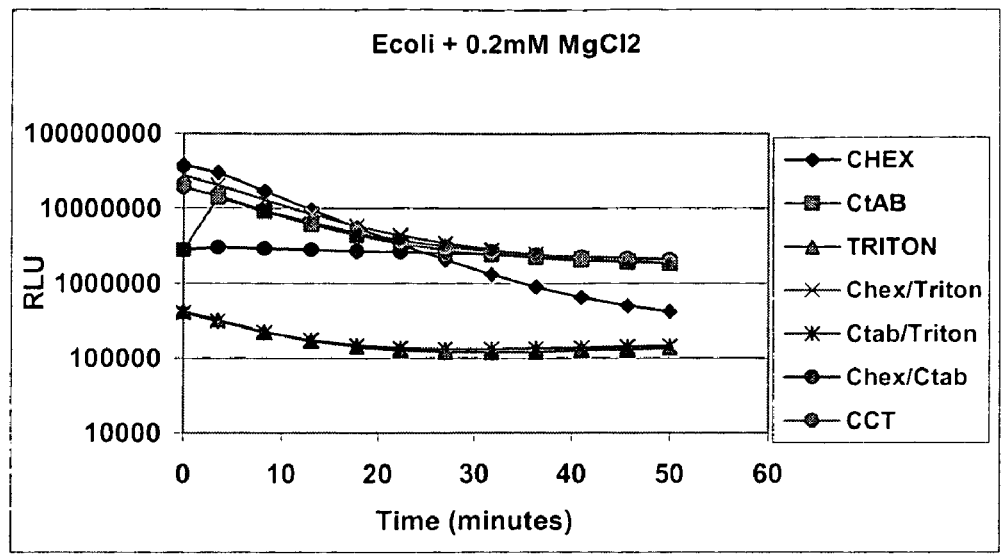
FIG. 6 is a graph depicting kinetics of ATP detection at low (0.2 mM) and high (20 mM) divalent cation concentrations using a panel of ATP extracting agents in $E.$ $coli$ (FIG. 6A, 6B) or $P.$ $aeruginosa$ (FIG. 6C, 6D). Purified ATP was used as a control in FIG. 6E, 6F.
Figure 6B:
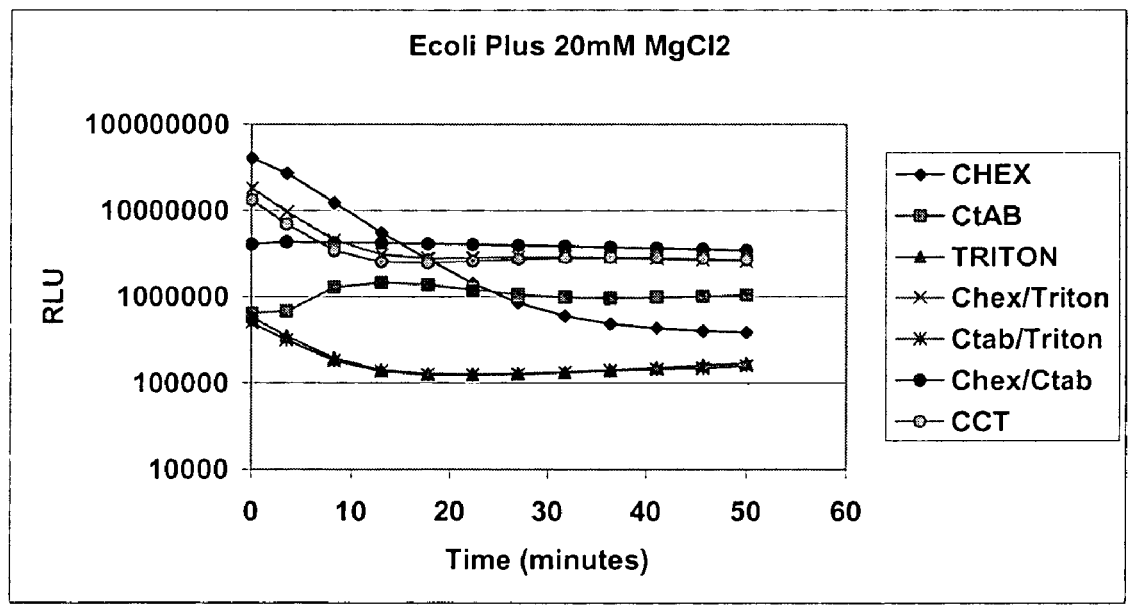
Figure 6C:
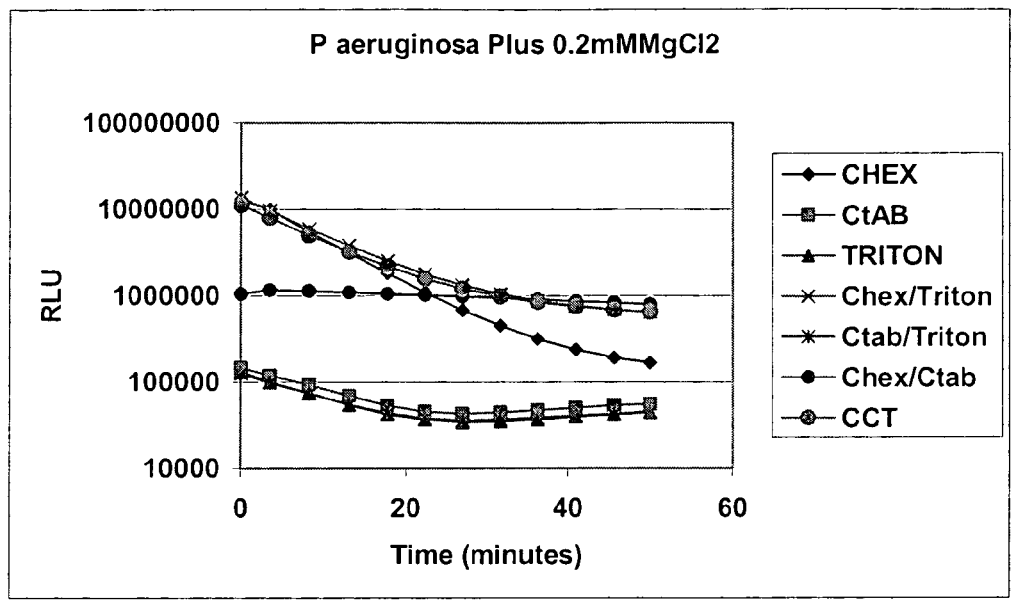
Figure 6D:
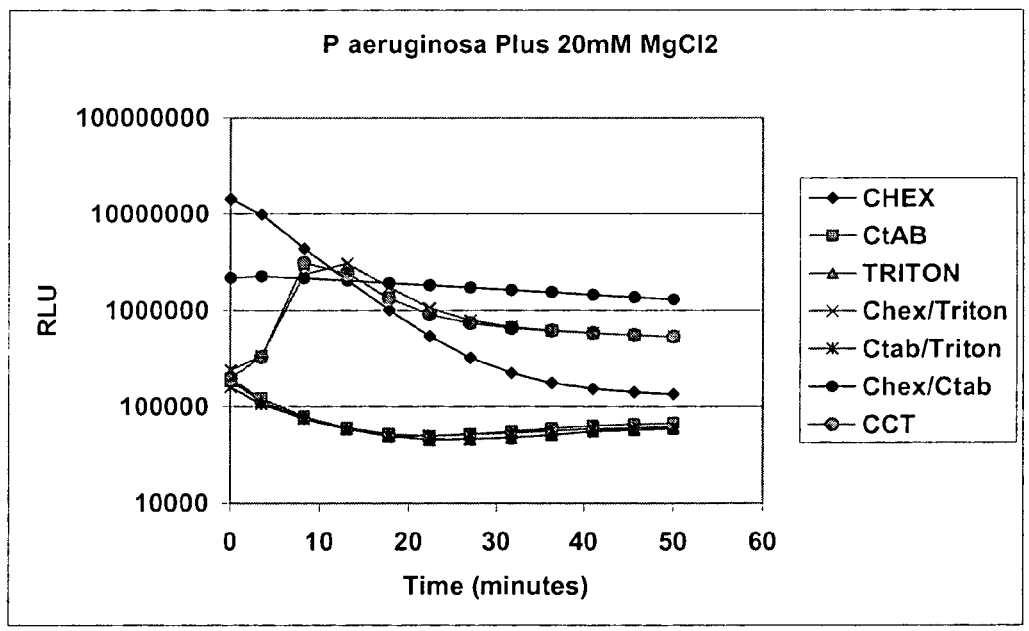
Figure 6E:
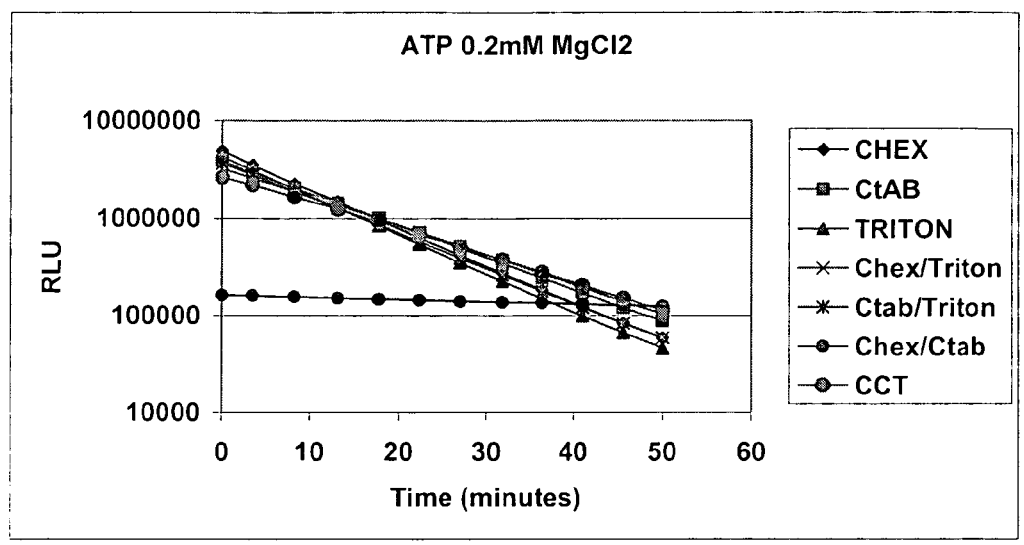
Figure 6F:
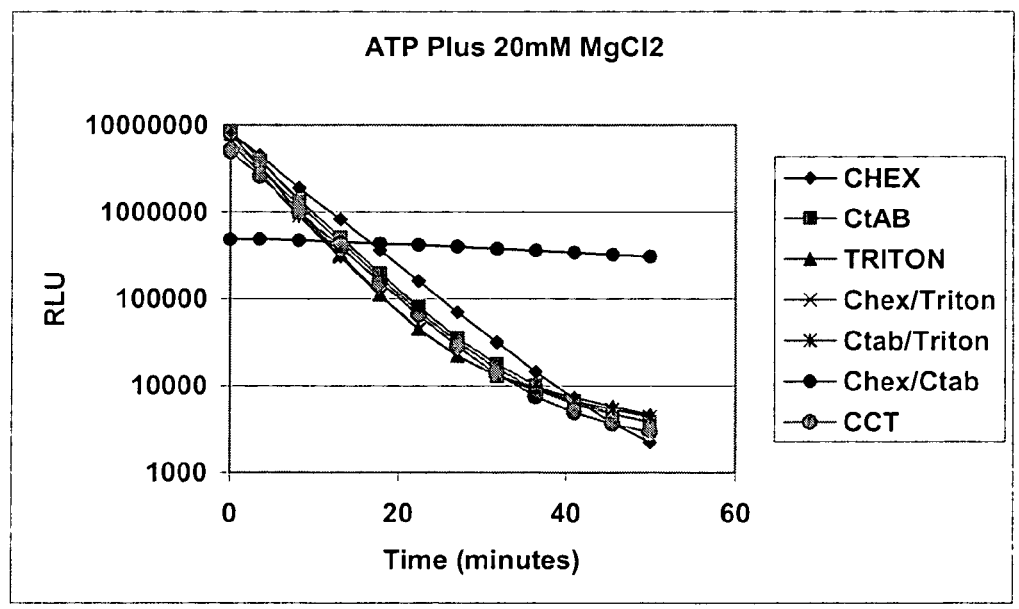

To evaluate the kinetics of ATP detection at low (0.2 mM) and high (20.0 mM) divalent cation concentrations, various different ATP extracting agent combinations were included in a reagent composition (200 mM HEPES (Sigma), 2 mM NaF (Sigma), 25 µM NaPPI (Sigma), 0.358 mg/ml UltraGlo™ Luciferase (Promega), and 6 mM beetle luciferin (Promega)) containing a low (0.2 mM) or high (20.0 mM) concentration of $MgCl_2$ to form a series of reagent compositions, each differing with regard to extracting agents and/or divalent cation concentrations contained therein. 100 µl of each of the different reagent compositions was added to 100 µl of *E. coli* (FIG. 6A, 6B), *P. aeruginosa* (FIG. 6C, 6D), or a $1\times10^{-9}$M ATP control solution (FIG. 6E, 6F) in a small well. Luminescence was measured periodically over a 50 minute time period. The results of this analysis (FIG. 6A-6F) indicate differences in the glo kinetics depending on the microbe, the ATP extractant combination, and the divalent cation concentration.

Example 7

Figure 7A:
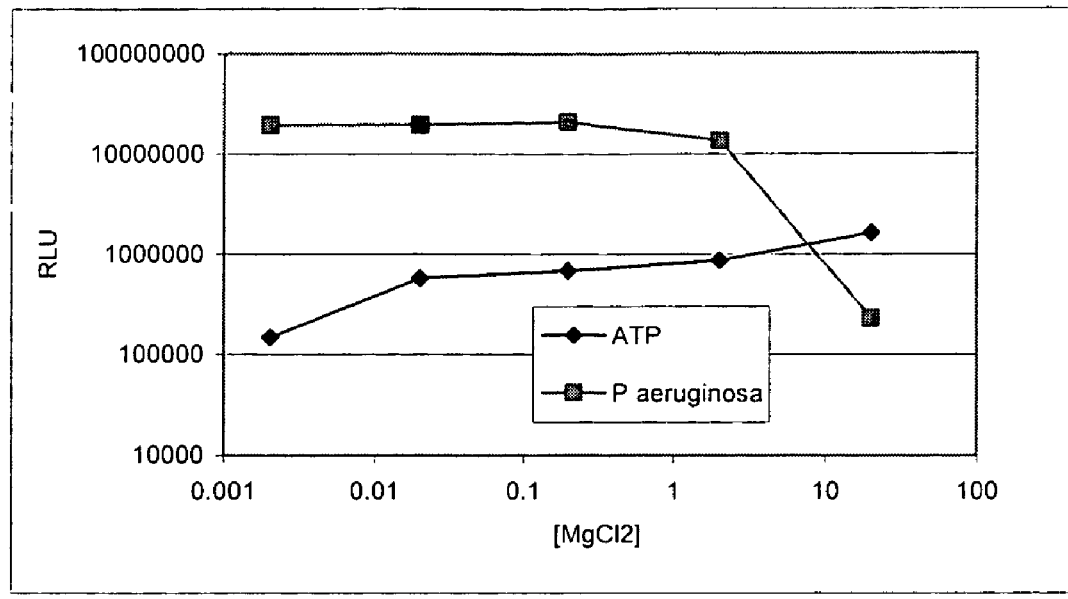
FIG. 7 is a graph depicting the effects of $Mg^{2+}$ (FIG. 7A), $Ca^{2+}$ (FIG. 7B) and $Mn^{2+}$ (FIG. 7C) on extraction and detection of ATP in $P.$ $aeruginosa$ at low (0.2 mM) and high (20 mM) divalent cation concentrations.
Figure 7B:
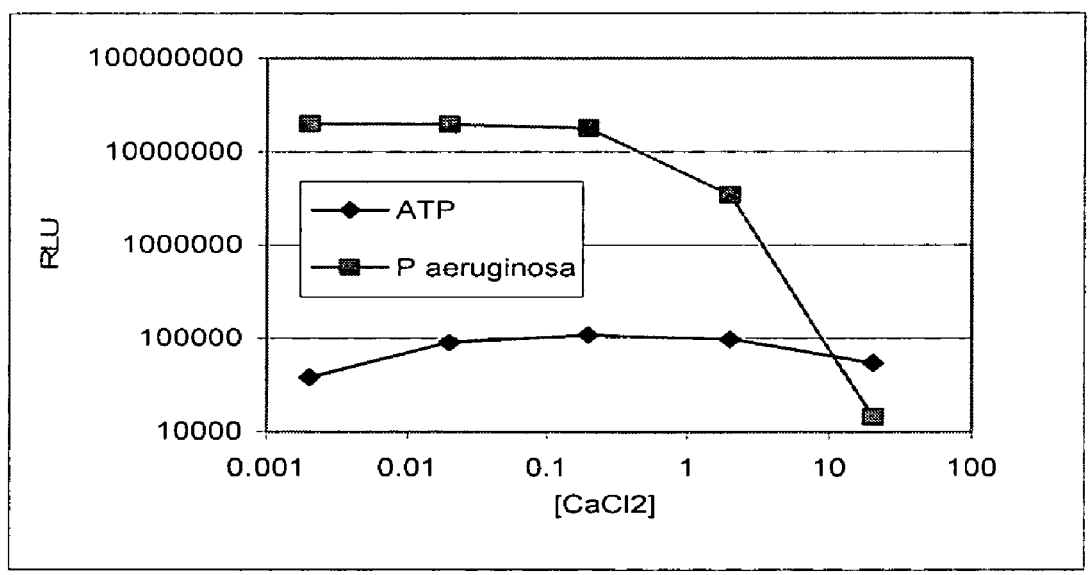
Figure 7C:
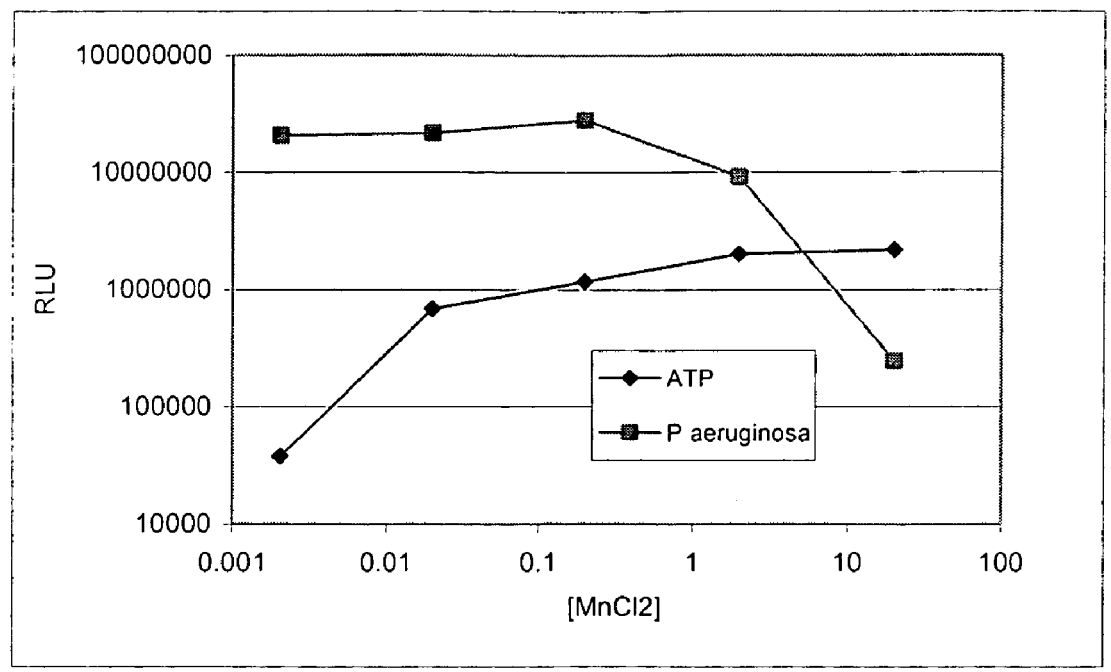

The Impact of Divalent Cations on Extraction and Detection of ATP is Not Limited to $Mg^{2+}$ To evaluate the effects of alternate divalent cations on ATP extraction and detection at low (0.2 mM) and high (20 mM) divalent cation concentrations, *Pseudomonas aeruginosa* (ATCC27853) was grown in Mueller Hinton II (MH II) Broth at 37° C. overnight. The overnight culture was diluted 50-fold in fresh MH II Broth and then incubated for several hours to reach log phase. Cells were diluted to approximately $1\times10^6$ cells per well. An ATP control solution was diluted to approximately $10^{-9}$ M. 100 µl of a BacTiter-Glo™ reagent composition (200 mM HEPES (Sigma), 0.08% CTAB (Sigma), 0.16% CHEX (Sigma), 1% Triton-X100 (Sigma), 2 mM NaF (Sigma), 25 µM NaPPI (Sigma), 0.358 mg/ml UltraGlo™ Luciferase (Promega), and 6 mM beetle luciferin (Promega) containing varying concentrations of either $MgCl_2$ (FIG. 7A), $CaCl_2$ (FIG. 7B), or $MnCl_2$ (FIG. 7C) at 0.002, 0.02, 0.2, 2.0 or 20 mM was prepared and added to 100 µl of the bacterial or ATP control samples. Luminescence was recorded on a Veritas™ Microplate Luminometer from Turner Biosystems. The results of this analysis (FIG. 7A-7C) indicate that the impact of divalent cations on extraction and detection of ATP is not limited to $Mg^{2+}$, since the use of high $Ca^{2+}$ (FIG. 7B) and $Mn^{2+}$ (FIG. 7C) was similarly found to impede ATP detection.

Example 8

The Impact of Divalent Cations on Extraction and Detection of ATP is Not Limited to Thermostable Luciferases

Figure 8:
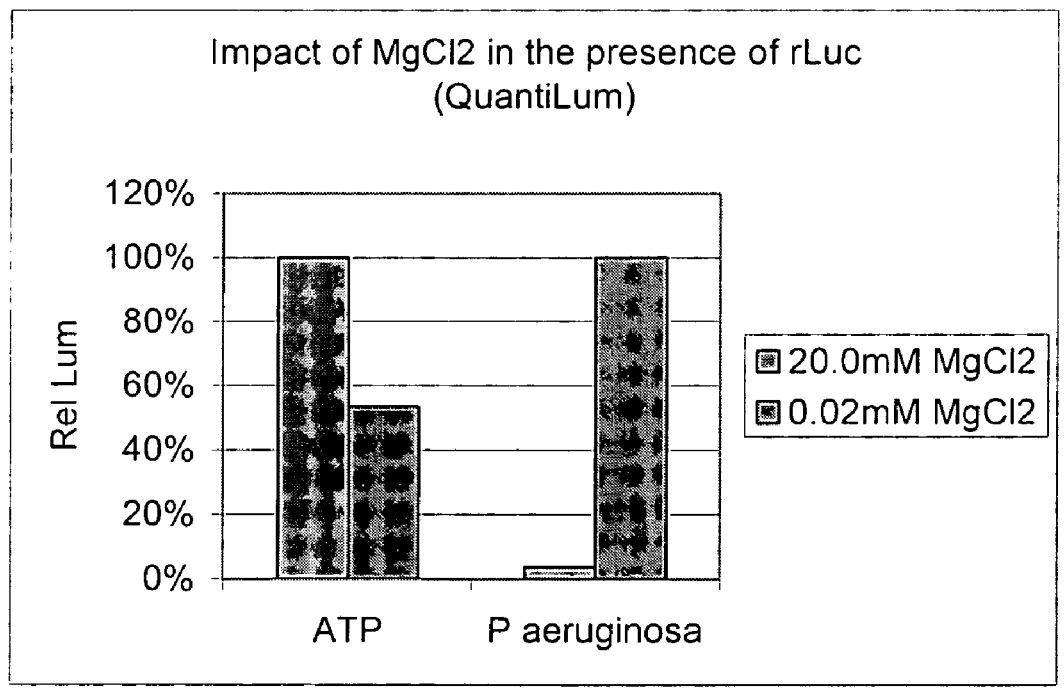
FIG. 8 is a graph depicting ATP detection in $P.$ $aeruginosa$ at low (0.2 mM) and high (20 mM) divalent cation concentrations using recombinant firefly luciferase (rather than a thermostable luciferase).

*Pseudomonas aeruginosa* (ATCC27853) was grown in Mueller Hinton II (MH II) Broth at 37° C. overnight. The overnight culture was diluted 50-fold in fresh MH II Broth and then incubated for several hours to reach log phase. Cells were diluted to approximately $1\times10^6$ cells per well. An ATP control solution was diluted to approximately $10^{-9}$M. 100 µl of a BacTiter-Glo™ reagent composition (200 mM HEPES (Sigma), 0.08% CTAB (Sigma), 0.]16% CHEX (Sigma), 1% Triton-X100 (Sigma), 2 mM NaF (Sigma), 25 µM NaPPI (Sigma), 0.358 mg/ml QUANTILUM™ Recombinant Luciferase (Promega), and 6 mM beetle luciferin (Promega) containing either low (0.2 mM) or high (20 mM) $MgCl_2$ concentrations was prepared and added to either the bacterial or the ATP control sample. Luminescence was recorded on a Veritas™ Microplate Luminometer from Turner Biosystems. The results of this analysis (FIG. 8) indicate that the inhibitory effects of divalent cations on single-step extraction and detection of ATP is not limited to the use of thermostable luciferases.

Example 9

Correlation Between Microbial Cell Number and Bioluminescent Signal

Four bacterial strains were used to evaluate the relationship between microbial cell number and luminescence. Bacterial strains *Escherichia coli* (ATCC25922), *Staphylococcus aureus* (ATCC25923), *Pseudomonas aeruginosa* (ATCC27853) and *Bacillus cereus* (ATCC10987) were grown in Mueller Hinton II (MH II) Broth at 37° C. overnight. The overnight culture was diluted 50-fold in fresh MH II Broth and then incubated for several hours to reach log phase. Samples of the culture were serially diluted using MH II Broth in a 96-well plate. A reconstituted BacTiter-Glo™ reagent composition (200 mM HEPES (Sigma), 0.08% CTAB (Sigma), 0.16% CHEX (Sigma), 1% Triton-X100 (Sigma), 20 mM $MgCl_2$, 23 mM EDTA, 2 mM NaF (Sigma), 25 µM NaPPI (Sigma), 0.358 mg/ml UltraGlo™ Luciferase (Promega), and 6 mM beetle luciferin (Promega)) was equilibrated for 1.5 hours at room temperature for improved sensitivity and added to each of the different culture samples. Luminescence was recorded on a Veritas™ Microplate Luminometer from Turner Biosystems (Sunnyvale, Calif.).

Figure 9:
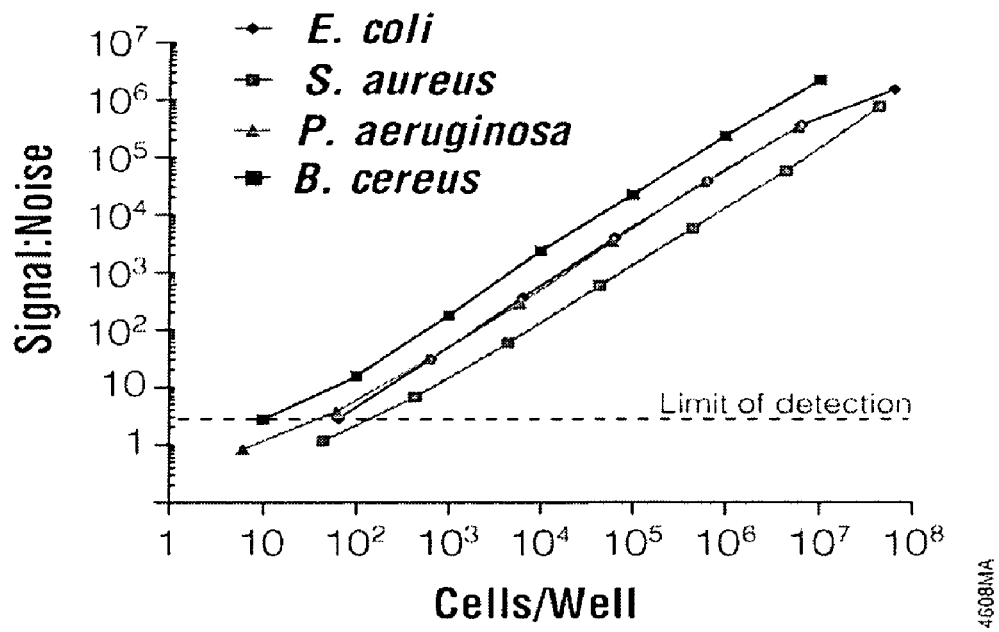
FIG. 9 is a graph depicting a correlation between bacterial cell numbers and luminescence in four bacterial strains ($E.$ $coli,$ $S.$ $aureus,$ $P.$ $aeruginosa,$ and $B.$ $cereus$).

The results of this analysis are shown in FIG. 9, which is a graph depicting a correlation between bacterial cell numbers and bioluminescence. Luminescent signals represent the mean of three replicates for each measurement. Bacterial cell numbers were determined by plate counting of colony forming units on Luria-Bertani agar plates. The signal-to-noise ratio was calculated where S:N=[mean of signal-mean of background]/standard deviation of background]. FIG. 9 demonstrates a linear correlation between luminescent signal and the number of cells over five orders of magnitude. The limits of detection drawn from this experiment for *E. coli*, *S. aureus*, *P. aeruginosa* and *B. cereus* are approximately 40, 150, 70 and 10 cells, respectively.

Example 10

BacTiter-Glo™ Assay Generates a Stable, Glow-Type Luminescent Signal

Figure 10:
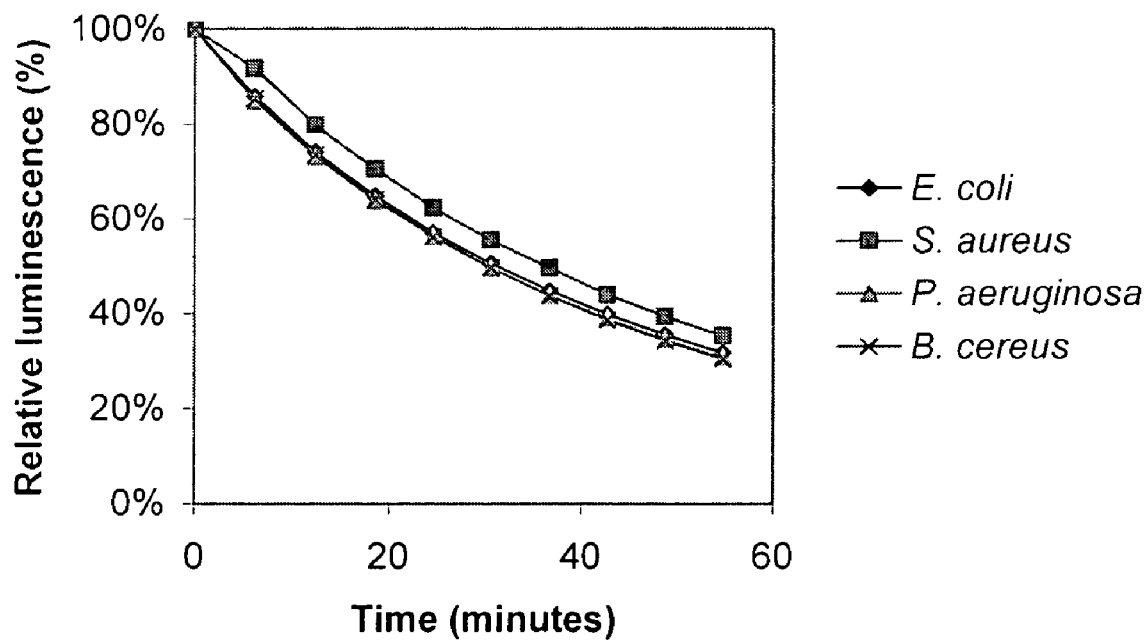
FIG. 10 is a graph depicting the duration of the luminescent signal produced with the microbial ATP assay.

Four different bacteria (*E. coli*, *S. aureus*, *P. aeruginosa* and *B. cereus*) were grown and assayed as described in Example 9. Approximately $10^6$ cells were used in each assay. The stability of the luminescent signal was monitored over time. Luminescence was recorded on a Veritas™ Microplate Luminometer from Turner Biosystems (Sunnyvale, Calif.). The results of this analysis (FIG. 10) indicate that a microbial assay system of the present invention can produce a stable, "glow-type" luminescent signal with a half-life ($T_{1/2}$) of >30 min in a range of microbial cells.

Example 11

BacTiter-Glo™ Assay Provides Enhanced Bioluminescent Detection of Bacterial Growth as a Function of Time

Figure 11:
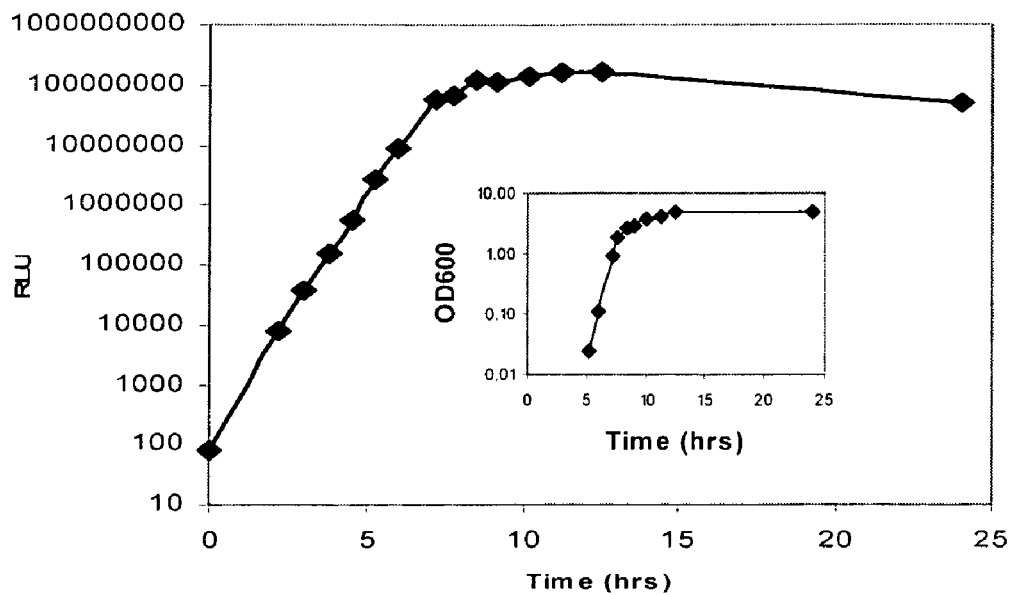
FIG. 11 is graph depicting the sensitivity of ATP detection for monitoring growth of $E.$ $coli.$

*E. coli* ATCC 25922 strain was grown in MH II Broth at 37° C. overnight. The overnight culture was diluted $1:10^6$ in 50 ml of fresh MH II Broth and incubated at 37° C. with shaking at 250 rpm. Samples were taken at various time points, and a luciferase detection assay was performed as described in Example 9. Luminescence was recorded on a Veritas™ Microplate Luminometer. Optical density was measured at 600 nm (O.D. 600) using a Beckman DU650 spectrophotometer. Diluted samples were used when readings of RLU and O.D. exceeded $10^8$ and 1, respectively. The results of this analysis (FIG. 11) indicate that the ATP detection assay provides a more sensitive measure of bacterial growth than conventional optical density measurements (compare results with inset).

Example 12

Screening Antimicrobial Compounds in a 96-Well Plate as a Function of Reduced Luminescence at t=5 hr

Figure 12:
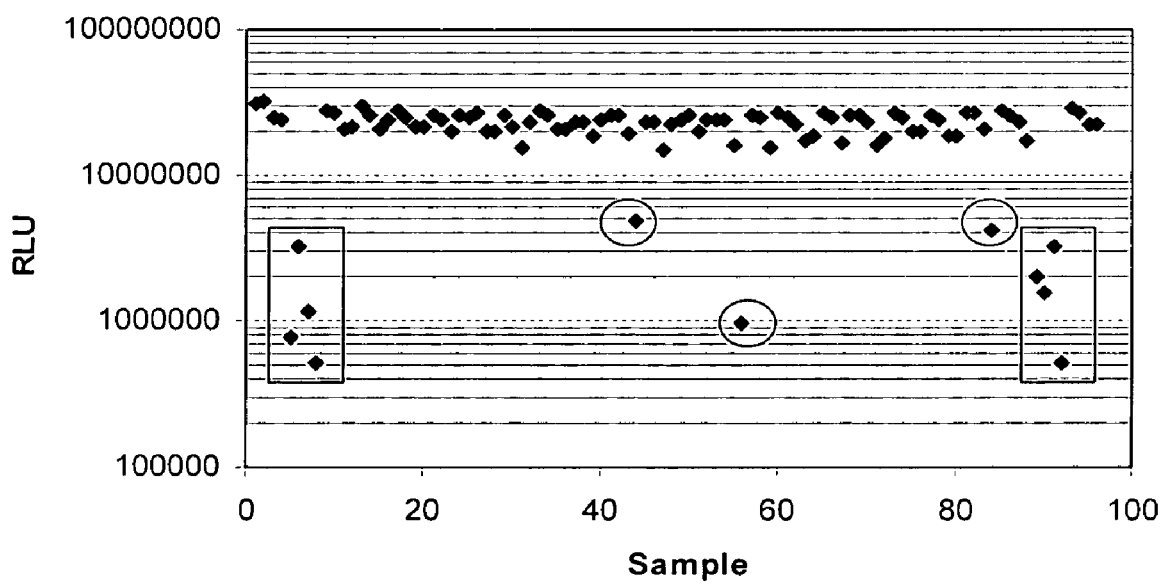
FIG. 12 is a graph depicting screening antimicrobial compounds in a 96-well plate as a function of reduced luminescence at t=5 hr.

*S. aureus* ATCC 25923 strain was grown in MH II Broth at 37° C. overnight. The overnight culture was diluted 100-fold in fresh MH II Broth and used as inoculum for the antimicrobial screen. Working stocks (50×) of LOPAC compounds and standard antibiotics were prepared in DMSO. Each well of the 96-well multiwell plate contained 245 µl of the inoculum and 5 µl of the 50× working stock. The multiwell plate was incubated at 37° C. for 5 hours. One hundred microliters of the culture was taken from each well, and the luciferase detection assay was performed as described in Example 9. Luminescence was measured using a Veritas™ Microplate Luminometer from Turner Biosystems (Sunnyvale, Calif.). The samples and concentrations are: Wells 1-4 and 93-96, negative control of 2% DMSO, wells 5-8 and 89-92, positive controls of 32 µg/ml standard antibiotics tetracycline, ampicillin, gentamicin, chloramphenicol, oxacillin, kanamycin, piperacillin, and erythromycin; wells 9-88, LOPAC compounds at 10 µM. The results of this analysis (FIG. 12), validate the use of this screening method for identifying antibiotic agents (denoted by circles as compared to positive controls, which are boxed).

Example 13

Bioluminescent Detection of Bacterial Growth as a Function of Antibiotic Dose Exposure

Figure 13:
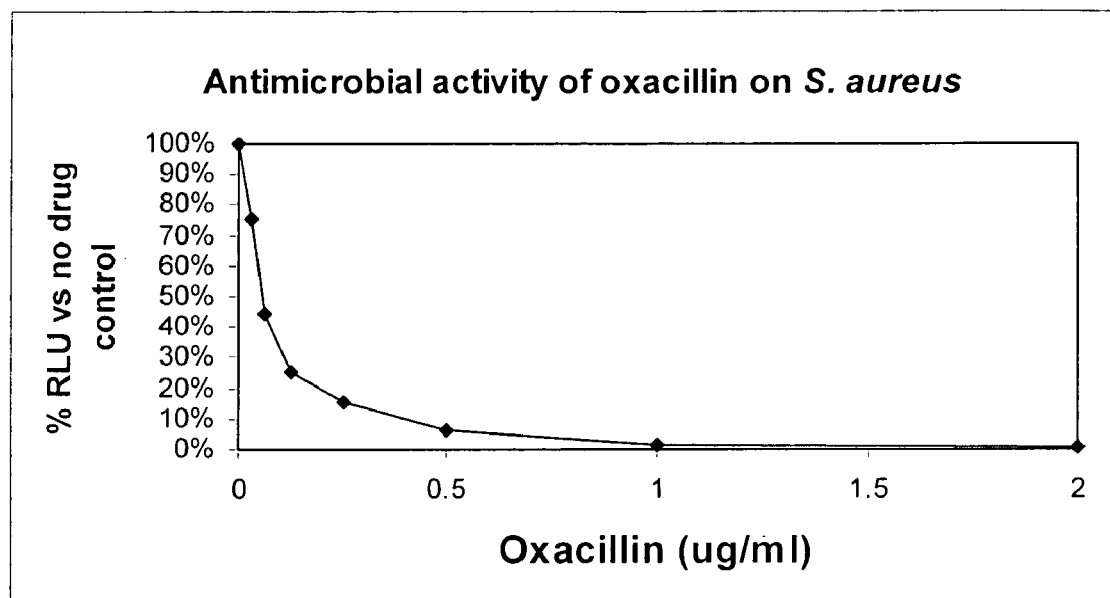
FIG. 13 is a graph depicting bioluminescent detection of bacterial growth as a function of antibiotic dose.

*S. aureus* ATCC 25923 strain and oxacillin were prepared as described in Example 8 and incubated at 37° C.; the ATP detection assay was performed after 19 hours of incubation as recommended for MIC determination by NCCLS (6). The relative percentage of RLU compared to the no-oxacillin control is shown. Luminescence was recorded on a Veritas™ Microplate Luminometer from Turner Biosystems (Sunnyvale, Calif.). The results of this analysis (FIG. 13) demonstrate a dose-dependent effect of antibiotics on ATP detection.

The invention claimed is:

1. A composition for extracting ATP from a gram negative microorganism comprising:
   (a) a reaction buffer;
   (b) one or more ATP extracting agents;
   (c) a divalent cation at a first concentration; and
   (d) a divalent cation chelator at a second concentration;
   wherein the first concentration is at least 10 mM and the second concentration is at least about equal to or greater than the first concentration.

2. The composition of claim 1, wherein the first concentration is at least 20 mM.

3. The composition of claim 1, wherein the first concentration is at least about 20 mM and the second concentration is at least about 20 mM.

4. An aqueous composition for detecting ATP in a sample suspected of containing a microorganism comprising:
   (a) a reaction buffer;
   (b) one or more ATP extracting agents;
   (c) a divalent cation at a first concentration (d) a divalent cation chelator at a second concentration; and (e) a luciferase enzyme wherein the second concentration is at least 10 mM and the difference between the first concentration and the second concentration is less than about 5 mM; and wherein the one or more ATP extracting agents comprises a compound or combination of compounds capable of disrupting the integrity of a bacterium or yeast to effect release of ATP therefrom.

5. The composition of claim 4, wherein the difference between the first concentration and the second concentration is less than about 2.5 mM.

6. The composition of claim 4, wherein the difference between the first concentration and the second concentration is less than about 1.0 mM.

7. The composition of claim 4, wherein the second concentration is greater than the first concentration.

8. The composition of claim 4, wherein the first concentration is at least about 20 mM and the second concentration is greater than about 20 mM.

9. The composition of claim 4, wherein the bacterium is a gram negative bacterium.

10. The composition of claim 4, wherein the one or more ATP extracting agents comprises cetyltrimethylammonium bromide.

11. The composition of claim 4, wherein the one or more one ATP extracting agents comprises chlorohexidine and a non-ionic detergent.

12. The composition of claim 4, wherein the one or more ATP extracting agents comprises cetyltrimethylammonium bromide, chlorohexidine, and a non-ionic detergent.

13. The composition of claim 4, wherein the divalent cation is $Mg^{2+}$, $Ca^{2+}$ or $Mn^{2+}$.

14. The composition of claim 4, wherein the divalent cation chelator is EDTA or CDTA.

15. The composition of claim 4, wherein the divalent cation is $Mg^{2+}$ and the divalent cation chelator is EDTA.

16. An aqueous composition for detecting ATP in a sample suspected of containing a microorganism comprising:

(a) a reaction buffer;

(b) one or more ATP extracting agents;

(c) a divalent cation at a first concentration;

(d) a divalent cation chelator at a second concentration;

wherein the second concentration is greater than the first concentration. wherein the first concentration is at least 10 mM and the difference between the first concentration and the second concentration is less than about 5 mM; and wherein the one or more ATP extracting agents comprises a compound or combination of compounds capable of disrupting the integrity of a bacterium or yeast to effect release of ATP therefrom.

17. The composition of claim 16, wherein the difference between the first concentration and the second concentration is less than about 2.5 mM.

18. The composition of claim 16, wherein the difference between the first concentration and the second concentration is less than about 1.0 mM.

19. The composition of claim 16, wherein the first concentration is at least about 20 mM and the second concentration is greater than about 20 mM.

20. The composition of claim 16, wherein the bacterium is a gram negative bacterium.

21. The composition of claim 16, wherein the one or more ATP extracting agents comprises cetyltrimethylammonium bromide.

22. The composition of claim 16, wherein the one or more one ATP extracting agents comprises chlorohexidine and a non-ionic detergent.

23. The composition of claim 16, wherein the one or more ATP extracting agents comprises cetyltrimethylammonium bromide, chlorohexidine, and a non-ionic detergent.

24. The composition of claim 16, wherein the divalent cation is $Mg^{2+}$, $Ca^{2+}$ or $Mn^{2+}$.

25. The composition of claim 16, wherein the divalent cation chelator is EDTA or CDTA.

26. The composition of claim 16, wherein the divalent cation is $Mg^{2+}$ and the divalent cation chelator is EDTA.

\* \* \* \* \*

UNITED STATES PATENT AND TRADEMARK OFFICE
CERTIFICATE OF CORRECTION

| | | |
|---|---|---|
| PATENT NO. | : 7,422,868 B2 | Page 1 of 1 |
| APPLICATION NO. | : 11/173092 | |
| DATED | : September 9, 2008 | |
| INVENTOR(S) | : Frank Fan | |

It is certified that error appears in the above-identified patent and that said Letters Patent is hereby corrected as shown below:

On the Title Page:

The first and sole Notice should read --

Subject to any disclaimer, the term of this patent is extended or adjusted under 35 U.S.C 154(b) by 104 days.

Signed and Sealed this
Eighteenth Day of January, 2011

David J. Kappos
*Director of the United States Patent and Trademark Office*